US006054487A

United States Patent [19]
Sekut et al.

[11] Patent Number: 6,054,487
[45] Date of Patent: Apr. 25, 2000

[54] METHODS AND COMPOSITIONS FOR MODULATING RESPONSIVENESS TO CORTICOSTEROIDS

[75] Inventors: Les Sekut, Westborough; Adam Carter, Newburyport; Tariq Ghayur, Grafton; Subhashis Banerjee, Shrewsbury; Daniel E. Tracey, Harvard, all of Mass.

[73] Assignee: BASF Aktiengesellschaft, Rheinland Pfalz, Germany

[21] Appl. No.: 08/820,692

[22] Filed: Mar. 18, 1997

[51] Int. Cl.⁷ .................................................. A61K 31/18
[52] U.S. Cl. ........................ 514/604; 514/602; 514/603
[58] Field of Search .................................. 514/604, 602, 514/603

[56] References Cited

U.S. PATENT DOCUMENTS

| | | | |
|---|---|---|---|
| 3,320,125 | 5/1967 | Grim | 167/54 |
| 5,411,985 | 5/1995 | Bills et al. | 514/460 |
| 5,416,013 | 5/1995 | Black et al. | 435/226 |
| 5,430,128 | 7/1995 | Chapman et al. | 530/330 |
| 5,434,248 | 7/1995 | Chapman et al. | 530/330 |
| 5,536,657 | 7/1996 | Chua et al. | 435/252.3 |
| 5,565,430 | 10/1996 | Dolle et al. | 514/19 |
| 5,656,627 | 8/1997 | Bemis et al. | 514/221 |

FOREIGN PATENT DOCUMENTS

| | | |
|---|---|---|
| 0 416 950 A1 | 3/1991 | European Pat. Off. . |
| 0 433 827 | 6/1991 | European Pat. Off. . |
| 0 519 748 | 12/1992 | European Pat. Off. . |
| 0 547 699 | 6/1993 | European Pat. Off. . |
| 0 638 644 | 2/1995 | European Pat. Off. . |
| WO 90/05147 | 5/1990 | WIPO . |
| WO 92/16226 | 10/1992 | WIPO . |
| WO 93/05071 | 3/1993 | WIPO . |
| WO 93/11743 | 6/1993 | WIPO . |
| WO 93/14777 | 8/1993 | WIPO . |
| WO 93/15741 | 8/1993 | WIPO . |
| WO 93/16710 | 9/1993 | WIPO . |
| WO 94/03153 | 2/1994 | WIPO . |
| WO 95/24918 | 9/1995 | WIPO . |
| WO 95/35308 | 12/1995 | WIPO . |
| WO 96/19968 | 7/1996 | WIPO . |
| WO 96/32345 | 10/1996 | WIPO . |
| WO 96/40093 | 12/1996 | WIPO . |

OTHER PUBLICATIONS

Deitzman et al., Acta Chir. Belg., 72(4), 308–30 (Abstract), 1973.
Almqvist et al., Acta Chir. Scand., Suppl., 526, 120–3 (Abstract), 1985.
Antin, J.H. et al., "Recombinant human interleukin–1 receptor antagonist in the treatment of steroid–resistant graft–versus–host disease" *Blood* 84(4):1342–1348 (1994).
Banner, K.H. et al., "The effect of selective phosphodiesterase 3 and 4 isoenzyme inhibitors and established anti–asthma drugs on inflammatory cell activation" *British Journal of Pharmacology* 119:1255–1261 (1996).
Baxter, J.D., "The effects of glucocorticoid therapy" *Hospital Practice* 27(9):111–18, 123–134 (1992).
Bazan, J.F. et al., "A newly defined interleukin–1?" *Nature* 379:591 (1996).
Cerretti, D. P. et al., "Molecular cloning of the interleukin–1β converting enzyme" *Science* 256:97–100 (1992).
Chizzonite, R. et al., "IL–12: monoclonal antibodies specific for the 40–kDa subunit block receptor binding and biologic activity on activated human lymphoblasts" *The Journal of Immunology* 147:1548–1556 (1991).
Cohan, V.L. et al., "In vitro pharmacology of the novel phosphodiesterase type 4 inhibitor, CP–80633" *The Journal of Pharmacology and Experimental Therapeutics* 278:1356–1361 (1996).
Dolle, R.E. et al., "$P_1$ aspartate–based peptide α–((2, 6–Dichlorobenzoyl)oxy)methyl ketones as potent time–dependent inhibitors of interleukin–1β–converting enzyme" *J. Med. Chem.* 37:563–564 (1994).
Gately, M.K, et al., "Interleukin–12 antagonist activity of mouse interleukin–12 p40 homodimer in vitro and in vivo" *Annals New York Academy of Sciences* 795:1–12 (1996).
Geiger, T. et al., "Inteferon–γ overcomes the glucocorticoid–mediated and the interleukin–4 mediated inhibition of interleukin–1β synthesis in human monocytes" *Lymphokine and Cytokine Research* 12(5):271–278 (1993).
Gillessen, S. et al., "Mouse interleukin–12 (IL–12) p40 homodimer: a potent IL–12 antagonist" *Eur. J. Immunol.* 25:200–206 (1995).
Gu, Y. et al., "Activation of interferon–γ inducing factor medicated by interleukin 1β converting enzyme" *Science* 275:206–209 (1997).

(List continued on next page.)

*Primary Examiner*—William R. A. Jarvis
*Attorney, Agent, or Firm*—Lahive & Cockfield, LLP

[57] ABSTRACT

Method for modulating responsiveness to corticosteroids in a subject are provided. In the method of the invention, an agent which antagonizes a factor that regulates production of IFN-γ in the subject is administered to the subject in combination with a corticosteroid such that responsiveness of the subject to the corticosteroid is modulated as compared to when a corticosteroid alone is administered to the subject. In one embodiment, the agent is an interferon-γ inducing factor (IGIF) antagonist. In another embodiment, the agent is an interleukin-12 (IL-12) antagonist. In a preferred embodiment, the agent is an inhibitor of a caspase family protease, preferably an ICE inhibitor. In another preferred embodiment, the agent is an anti-IL-12 monoclonal antibody. Other preferred agents include phosphodiesterase IV inhibitors and beta-2 agonists. The methods of the invention can be used in the treatment of a variety of inflammatory and immunological diseases and disorders. Pharmaceutical compositions comprising an agent which antagonizes a factor that regulates production of IFN-γ in a subject, a corticosteroid and a pharmaceutically acceptable carrier are also provided. A preferred composition comprises an ICE inhibitor, a corticosteroid and a pharmaceutically acceptable carrier.

46 Claims, 3 Drawing Sheets

OTHER PUBLICATIONS

Kam, J.C. et al, "Combination IL–2 and IL–4 reduces glucocorticoid receptor–binding affinity and T cell response to glucocorticoids" *The Journal of Immunology* 151:3460–3466 (1993).

Kaplan, M.H. et al., "Impaired IL–12 responses and enhanced development of Th2 cells in Stat4–deficient mice" *Nature* 382:174–177 (1996).

Kimberly, R.P., "Glucocorticoid therapy for rheumatic diseases" *Current Opinion in Rheumatology* 4:325–331 (1992).

Kimberly, R.P., "Mechanisms of action, dosage schedules, and side effects of steroid therapy" *Current Opinion in Rheumatology* 3:373–379 (1991).

Kuida, K. et al., "Altered cytokine export and apoptosis in mice deficient in interleukin–1β converting enzyme"*Science* 267:2000–2003 (1995).

Leonard, J.P. et al., "Prevention of experimental autoimmune encephalomyelitis by antibodies against interleukin 12" *J. Exp. Med.* 181:381–386 (1995).

Li, P. et al., "Mice deficient in IL–1β–converting enzyme are defective in production of mature IL–1 β and resistant to endotoxic shock" *Cell* 80:401–411 (1995).

Ling, P. et al., "Human IL–12 p40 homodimer binds to the IL–12 receptor but does not mediate biologic activity" *The Journal of Immunology* 154:116–127 (1995).

Luedke, C.E. et al., "Interferon–γ overcomes glucocorticoid suppression of cachectin/tumor necrosis factor biosynthesis by murine macrophages" *J Clin. Invest.* 86:1234–1240 (1990).

Neurath, M.N. et al., "Antibodies to interleukin 12 abrogate established experimental colitis in mice" *The Journal of Experimental Medicine* 182:1281–1290 (1995).

Okamura, H. et al., "Cloning of a new cytokine that induces IFN–γ production by T cells" *Nature* 378:88–91 (1995).

Presky, D.H. et al., "Immunoregulation by interleukin–12: IL 12 receptors and receptor antagonists" *Res. Immunol.* 146:439–445 (1995).

Schoenhaut, D.S. et al., "Cloning and expression of murine IL–12" *The Journal of Immunology* 148:3433–3440 (1992).

Sekut, L. et al., "Anti–inflammatory activity of phosphosiesterase (PDE)–IV inhibitors in acute and chronic models of inflammation" *Clin. Exp. Immunol.* 100:126–132 (1995).

Sekut, L. et al, "Anti–inflammatory activity of salmeterol: down–regulation of cytokine production" *Clin. Exp. Immunol.* 99:461–466 (1995).

Severn, A. et al., "Regulation of tumor necrosis factor production by adrenaline and β–adrenergic agonists" *The Journal of Immunology* 148:3441–3445 (1992).

Sjölin, J., "High–dose corticosteroid therapy in human septic shock: has the jury reached a correct verdict?" *Circulatory Shock* 35:139–151 (1991).

Thornberry, N.A. et al., "A novel heterodimeric cysteine protease is required for interleukin–1β processing in monocytes" *Nature* 356:768–774 (1992).

Thierfelder, W.E. et al., "Requirement for Stat4 in interleukin–12–mediated responses of natural killer and T cells" *Nature* 382:171–174 (1996).

Truhan, A.P. et al., "Corticosteroids: a review with emphasis on complications of prolonged systemic therapy" *Annals of Allergy* 62:375–391 (1989).

Ushio, S. et al., "Cloning of the cDNA for human IFN–γ–inducing factor, expression in *Escherichia coli,* and studies on the biologic activities of the protein" *The Journal of Immunology* 156:4274–4279 (1996).

van der Pouw Kraan, T.C.T.M. et al., "Prostaglandin–E2 is a potent inhibitor of human interleukin 12 production" *J. Exp. Med.* 181:775–779 (1995).

van Wauwe, J. et al., "Cytokine production by phytohemagglutinin–stimulated human blood cells: effects of corticosteroids, T cell immunosuppressants and phosphodiestrase IV inhibitors" *Inflamm. Res.* 44:400–405 (1995).

Weisman, M.H. et al., "Corticosteroids in the treatment of rheumatologic diseases" *Current Opinion in Rheumatology* 7:183–190 (1995).

METHODS AND COMPOSITIONS FOR MODULATING RESPONSIVENESS TO CORTICOSTEROIDS

BACKGROUND OF THE INVENTION

Standard therapy for a variety of immune and inflammatory disorders includes administration of corticosteroids, which have the ability to suppress immunologic and inflammatory responses. Corticosteroids are used in the treatment of disorders such as asthma, autoimmune diseases (e.g., rheumatoid arthritis, systemic lupus erythematosus) and transplant rejection (for reviews on corticosteroids, see e.g., Truhan, A. P. et al. (1989) *Annals of Allergy* 62:375–391; Baxter, J. D. (1992) *Hospital Practice* 27:111–134; Kimberly, R. P. (1992) *Curr. Opin. Rheumatol.* 4:325–331; Weisman, M. H. (1995) *Curr. Opin. Rheumatol.* 7:183–190). Corticosteroids are also used topically in the treatment of various dermatological disorders, such as contact dermatitis, psoriasis vulgaris, lichen planus, keloids and urticaria pigmentosa (for a review, see Sterry, W. (1992) *Arch. Dermatol. Res.* 284 (Suppl.):S27–S29).

While therapeutically beneficial, the use of corticosteroids is associated with a number of side effects, ranging from mild to possibly life threatening. Complications associated with prolonged and/or high dose steroid usage include musculoskeletal effects (e.g., osteoporosis, myopathy, aseptic necrosis of bone), ophthalmic effects (e.g., posterior subcapsular cataracts), gastrointestinal effects (e.g., ulcers, pancreatitis, nausea, vomiting), cardiovascular effects (e.g., hypertension, atherosclerosis), central nervous system effects (e.g., pseudotumor cerebri, psychiatric reactions), dermatological effects (e.g., hirsutism, redistribution of subcutaneous fat, impaired wound healing, thinning of the skin) and suppression of the hypothalamus-pituitary-adrenal axis (see e.g., Truhan, A. P. et al. (1989) *Annals of Allergy* 62:375–391). Many of the side effects of corticosteroid usage appear to be dose-dependent (Kimberly, R. P. (1992) *Curr. Opin. Rheumatol.* 4:325–331). Accordingly, methods and compositions that enable the use of a lower effective dosage of corticosteroids (referred to as the "steroid sparing effect") would be highly desirable to avoid unwanted side effects.

Another problem that limits the usefulness of corticosteroids is the phenomenon of steroid resistance. Certain inflammatory or immunological diseases exhibit refractoriness to steroid treatment. For example, attempts to use corticosteroid therapy to treat septic shock in humans have met with disappointing results and thus corticosteroids are not generally recommended as adjunctive therapy in severe sepsis or septic shock (see e.g., Putterman, C. (1989) *Israel J. Med. Sci.* 25:332–338; Bone, R. C. and Brown, R. C. (1990) in Vincent, J. L. (ed.) "*Update in Intensive Care and Emergency Medicine* 10", Heidelberg:Springer Verlag, p. 121). Other disorders that often exhibit resistance to corticosteroid treatment include inflammatory bowel disease (see e.g., Hibi, T. et al. (1995) *J. Gastroenterol.* 30:121–123) and graft-versus-host disease (Antin, J. H. et al. (1994) *Blood* 84:1342–1348; Racadot, E. et al. (1995) *Bone Marrow Transplantation* 15:669–677). Thus, methods and compositions that can be used to overcome or reverse corticosteroid resistance in inflammatory and immunological disorders are still needed.

Yet another disadvantage of corticosteroid therapy is the occurrence of a "steroid rebound effect" when corticosteroid administration is discontinued. A steroid rebound effect is characterized by the worsening of the inflammatory condition(s) being treated upon cessation of steroid therapy. Methods and compositions that can be used to ameliorate the steroid rebound effect are still needed.

SUMMARY OF THE INVENTION

This invention provides methods and compositions for modulating responsiveness to corticosteroids in a subject. For example, the methods and compositions of the invention can be used to reverse steroid resistance in a subject, to thereby allow the subject to be treated with corticosteroids. The methods and compositions of the invention also can be used to increase steroid sensitivity in a subject, to thereby achieve therapeutic effectiveness of corticosteroid treatment at lower dosages (e.g., to avoid harmful side effects of high doses of corticosteroids or to allow treatment of steroid-dependent diseases with lower doses). Still further, the methods and compositions of the invention can be used to ameliorate the steroid rebound effect when a subject undergoing corticosteroid treatment is taken off corticosteroids.

In the modulatory methods of the invention, an agent which antagonizes a factor that regulates production of IFN-γ in a subject is administered to the subject in combination with a corticosteroid such that responsiveness of the subject to the corticosteroid is modulated as compared to when a corticosteroid alone is administered to the subject. The agent is administered at a dosage and by a route sufficient to inhibit IFN-γ production in the subject. In various embodiments, the agent and the corticosteroid are administered at the same time, the agent is administered first and then the corticosteroid is administered or the corticosteroid is administered first and then the agent is administered. The methods can be applied to prophylactic and therapeutic regimens of corticosteroid treatment.

In one embodiment, the method involves administration of an agent that is an IFN-γ inducing factor (IGIF) antagonist. The IGIF antagonist is administered at a dosage and by a route sufficient to inhibit IGIF activity in the subject. The IGIF antagonist can act, for example, at the level of IGIF synthesis, IGIF cytokine activity or IGIF interaction with an IGIF receptor. In a preferred embodiment, the IGIF antagonist is an inhibitor of a caspase family protease, preferably an Interleukin-1β Converting Enzyme (ICE) inhibitor. In another embodiment, the IGIF antagonist is an antibody, antibody fragment or engineered binding protein that binds to IGIF or an IGIF receptor.

In another embodiment, the method involves administration of an agent that is an Interleukin-12 (IL-12) antagonist. The IL-12 antagonist is administered at a dosage and by a route sufficient to inhibit IL-12 activity in the subject. The IL-12 antagonist can act, for example, at the level of IL-12 synthesis, IL-12 cytokine activity or IL-12 interaction with an IL-12 receptor. In a preferred embodiment, the IL-12 antagonist is an antibody, antibody fragment or engineered binding protein that binds to IL-12 or an IL-12 receptor. In another preferred embodiment, the IL-12 antagonist is an agent that stimulates production of cyclic AMP (cAMP) in cells that produce IL-12. Examples of agent that can be used to stimulate cAMP include phosphodiesterase IV inhibitors and beta-2 agonists. In yet another embodiment, the IL-12 antagonist is a STAT4 inhibitor.

Another aspect of the invention pertains to a method for modulating responsiveness to corticosteroids in a subject, wherein an inhibitor of a caspase family protease, preferably ICE, is administered to the subject together with a corticosteroid, such that responsiveness of the subject to the corticosteroid is modulated as compared to when a corticosteroid alone is administered to the subject.

Yet another aspect of the invention pertains to a method for modulating responsiveness to corticosteroids in a subject, wherein an IL-12 antagonist is administered to the subject together with a corticosteroid, such that responsiveness of the subject to the corticosteroid is modulated as compared to when a corticosteroid alone is administered to the subject.

Still another aspect of the invention pertains to a method for modulating responsiveness to corticosteroids in a subject, wherein a subject in need of modulation of responsiveness to a corticosteroid is selected and an agent which antagonizes a factor that regulates production of IFN-γ in the subject is administered to the subject such that responsiveness of the subject to a corticosteroid is modulated as compared to when a corticosteroid alone is administered to the subject. The agent is administered to the subject at a dosage and by a route sufficient to inhibit IFN-γ production in the subject. The subject that is selected can be, for example, a subject that is steroid resistant prior to treatment, a steroid-responsive subject in whom steroid sensitivity is to be increased or a subject to be taken off steroids in whom the steroid rebound effect is to be ameliorated.

The invention also provides pharmaceutical compositions for modulating responsiveness to corticosteroids in a subject. In one embodiment, a composition of the invention comprises an agent which antagonizes a factor that regulates production of IFN-γ in the subject, a corticosteroid and a pharmaceutically acceptable carrier. In another embodiment, a composition of the invention comprises an IGIF antagonist (such as inhibitor of a caspase family protease, preferably an ICE inhibitor, or an anti-IGIF or anti-IGIF receptor monoclonal antibody), a corticosteroid and a pharmaceutically acceptable carrier. In yet another embodiment, a composition of the invention comprises an IL-12 antagonist (e.g., an anti-IL-12 or anti-IL-12 receptor monoclonal antibody, a phosphodiesterase IV inhibitor, a beta-2 agonist, a STAT4 inhibitor), a corticosteroid and a pharmaceutically acceptable carrier. The pharmaceutical compositions of the invention can be formulated for administration via a preferred route of administration for achieving a desired therapeutic effect. In one preferred embodiment, the pharmaceutical composition is formulated for topical administration. In another preferred embodiment, the pharmaceutical composition is formulated for administration by inhalation. Other preferred routes of administration include oral and intravenous administration.

The methods and compositions of the invention can be used in the treatment of any disease or disorder in which it is desirable to modulate steroid responsiveness. In a preferred embodiments, the methods and compositions of the invention are used to treat a subject suffering from septic shock. In another embodiment, the methods and compositions of the invention are used to treat a subject suffering from Crohn's disease. In another embodiment, the methods and compositions are used to treat a subject suffering from asthma. In another embodiment, the methods and compositions are used to treat a subject suffering from an autoimmune disease or disorder. In another embodiment, the methods and compositions are used to treat a subject suffering from graft-versus-host disease or transplant rejection. In yet another embodiment, the methods and compositions are used to treat a subject suffering from an acute inflammatory disorder. In still another embodiment, the methods and compositions are used to treat a subject suffering from a chronic inflammatory disorder.

DETAILED DESCRIPTION OF THE INVENTION

Figure 1:
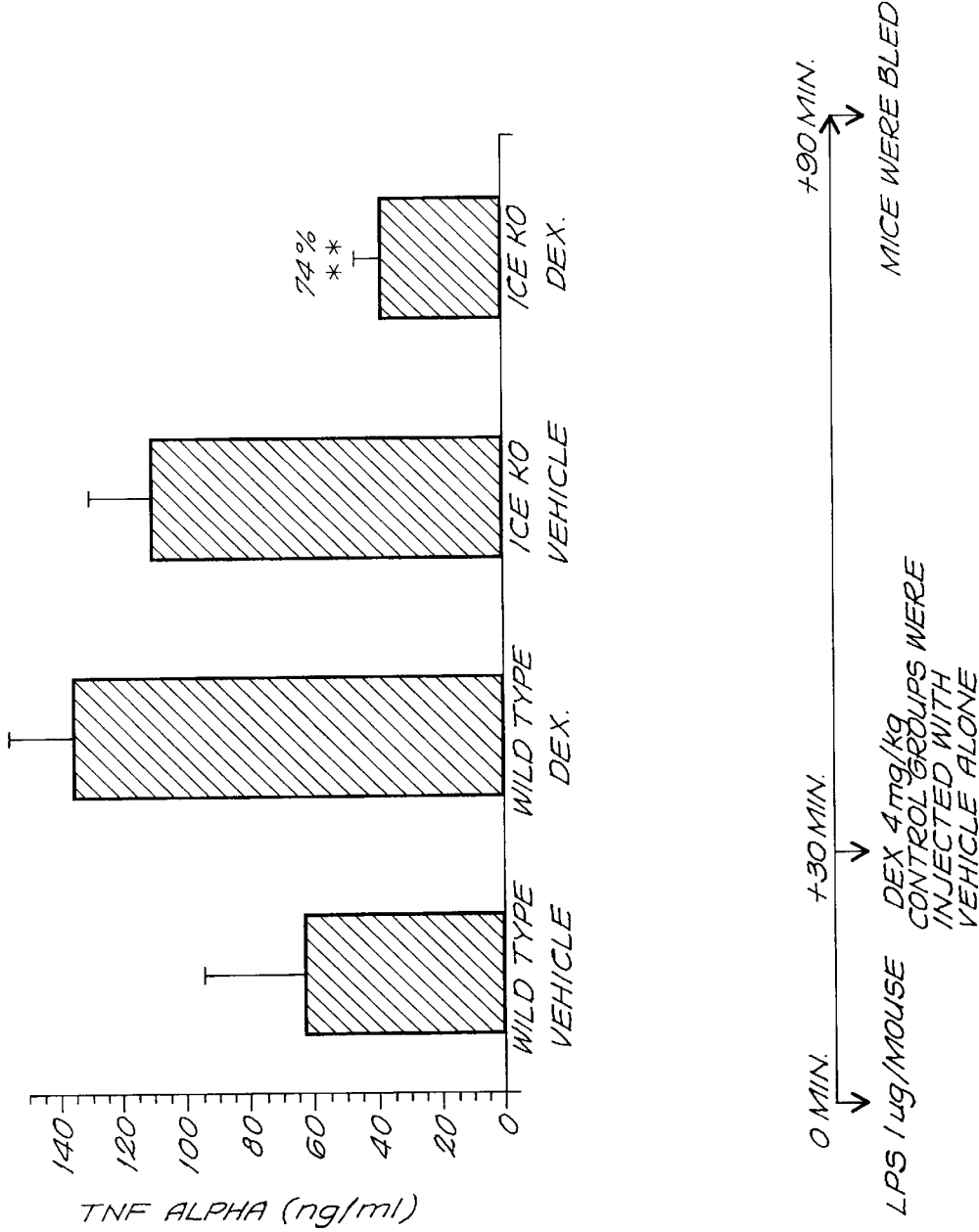
FIG. 1 is a bar graph showing serum TNFα levels (in ng/ml) in wild type and ICE-deficient (ICE KO) mice treated with vehicle alone or dexamethasone (4 mg/kg) 30 minutes after LPS in the LPS/P. acnes septic shock model, demonstrating that the ICE-deficient mice, but not wild type mice, exhibit suppression of TNFα production and hence are steroid responsive.

This invention is based, at least in part, upon the discovery that ICE deficient mice, in contrast to wild type control mice, are responsive to corticosteroids after LPS challenge in a septic shock model (see Example 1). Moreover, the ICE deficient mice show increased sensitivity to low doses of corticosteroids compared to wild type control mice, when corticosteroid treatment is given before LPS challenge in the septic shock model (see Example 2).

It has previously been described that administration of interferon-γ (IFN-γ) can overcome corticosteroid suppression of TNFα biosynthesis by murine macrophages (Leudke, C. E. and Cerami, A. (1990) *J. Clin. Invest.* 86:1234–1240). Moreover, ICE and other caspase family proteases can cleave the precursor form of Interferon-γ Inducing Factor (IGIF) to its mature, active form (see Example 4). Although not intending to be limited by mechanism, the ability to confer corticosteroid responsiveness by inhibiting ICE activity in a subject, in accordance with the present invention, is thought to result from inhibition of IGIF processing by ICE such that production of mature IGIF is inhibited, thereby leading to decreased production of IFN-γ in the subject.

In view of the foregoing, the invention broadly provides methods and compositions for modulating responsiveness to corticosteroids in which a factor that regulates production of IFN-γ is antagonized in a subject. This factor that regulates production of IFN-γ, and which is antagonized, can be IGIF (which can be antagonized, for example, by inhibiting ICE activity). Alternatively, another factor that regulates production of IFN-γ, such as IL-12, can be antagonized to thereby modulate corticosteroid responsiveness in the subject.

So that the invention may be more readily understood, a number of terms are first defined.

As used herein, the term "corticosteroid" refers to a class of therapeutic agents useful in treatment of inflammatory conditions, including those resulting from infection, transplant rejection and autoimmune disorders. Corticosteroids include those that are naturally occurring, synthetic, or semi-synthetic in origin, and are characterized by the presence of a steroid nucleus of four fused rings, for example, as found in cholesterol, dihydroxycholesterol, stigmasterol, and lanosterol structures. Corticosteroid drugs include cortisone, cortisol, hydrocortisone (11β17-dihydroxy-21-(phosphonooxy)-pregn-4-ene3,20-dione disodium), dihydroxycortisone, dexamethasone (21-(acetyloxy)-9-fluoro-11β, 17-dihydroxy- 16α-methylpregna-1,4-diene-3, 20-dione), and highly derivatized steroid drugs such as beconase (beclomethasone dipropionate, which is 9-chloro-11β,17,21, trihydroxy-16β-methylpregna-1,4 diene-3,20-dione 17,21-dipropionate). Other examples of corticosteroids include flunisolide, prednisone, prednisolone, methylprednisolone, triamcinolone, deflazacort and betamethasone.

The term "factor that regulates production of IFN-γ" is intended to include factors, other than IFN-γ itself, that directly or indirectly control the synthesis of IFN-γ in a subject. Examples of factors that regulate the production of IFN-γ include interferon-γ inducing factor (IGIF) (see e.g., Okamura, H. et al. (1995) Nature 378:88–91; Ushio, S. et al. (1996) J. Immunol. 156:4274–4279) and interleukin-12 (IL-12)(see e.g., Schoenhaut, D. et al. (1992) J. Immunol. 148:3433; PCT Publication WO 90/05147; European Patent Application EP 433 827 A2).

As used herein, agents that "antagonize" a factor are intended to include agents that inhibit the activity of the factor and agents that downregulate (i.e., inhibit) the synthesis or production of the factor.

The term "interferon-γ inducing factor (IGIF)" refers to a cytokine having an amino acid sequence as disclosed in Okamura, H. et al. (1995) Nature 378:88–91 (mouse) or Ushio, S. et al. (1996) J. Immunol. 156:4274–4279 (human), and other mammalian homologues thereof.

The term "IGIF antagonist" is intended to include agents that inhibit the synthesis or production of IGIF, agents that inhibit the activity of IGIF once synthesized, agents that inhibit the interaction of IGIF with an IGIF receptor and agents that inhibit the activity of an IGIF receptor. Examples of IGIF antagonists include inhibitors of caspase family proteases (e.g., ICE inhibitors) and antibodies, antibody fragments and engineered binding proteins that bind to either IGIF or an IGIF receptor.

The term "interleukin-12 (IL-12)" refers to a cytokine having an amino acid sequence as disclosed in Schoenhaut, D. et al. (1992) J. Immunol. 148:3433, PCT Publication WO 90/05147; and European Patent Application EP 433 827 A2, and other mammalian homologues thereof.

The term "IL-12 antagonist" is intended to include agents that inhibit the synthesis or production of IL-12, agents that inhibit the activity of IL-12 once synthesized, agents that inhibit the interaction of IL-12 with an IL-12 receptor and agents that inhibit the activity of an IL-12 receptor. Examples of IL-12 antagonists include antibodies, antibody fragments and engineered binding proteins that bind to either IL-12 or an IL-12 receptor, agents that stimulate intracellular production of cAMP in cells that produce IL-12 (such as phosphodiesterase IV inhibitors or beta-2 agonists) and agents that inhibit STAT4.

The term "caspase family protease" is intended to include members of the caspase proteases as described in Alnemri, E. et al. (1996) Cell 87:171, including caspase-1 (ICE), caspase-2 (ICH-1), caspase-3 (CPP32, Yama, apopain), caspase-4 (TX, ICH-2, $ICE_{rel}$-II), caspase-5 ($ICE_{rel}$-III, TY), caspase-6 (Mch2), caspase-7 (Mch3, ICE-LAP3, CMH-1), caspase-8 (MACH, FLICE, Mch5), caspase-9 (ICE-LAP6, Mch6) and caspase-10 (Mch4). Furthermore, a "caspase family protease" is intended to include any protein that shares greater than 20% amino acid sequence identity with ICE in the active domains of the protease (i.e., active domains of the p10 and p20 subunits of ICE), contains the peptide sequence glutamine-alanine-cysteine-X-glycine (QACXG), wherein the cysteine (C) is the catalytically active cysteine residue and X denotes any amino acid, and contains the sequence serine-histidine-glycine (SHG), located N-terminal to the QACXG motif, in which the histidine (H) is the catalytically essential histidine residue. Caspase family proteases typically demonstrate a strong preference for hydrolysis of peptide bonds immediately following an acidic amino acid (i.e., aspartic acid or glutamic acid).

Caspase family proteases are known in humans and other organisms including mice and Caenorhabditis elegans. Examples of caspase family proteases include, for example, Ich-1 (Wang, L. et al. (1994) Cell 78:739–750); ICH-2 (Kamens, J. et al. (1995) J. Biol. Chem. 270:15250–15256); Mch2 (Fernandes-Alnemri, T. et al. (1995) Cancer Res. 55:2737–2742); CPP32 (Femandes-Alnemri, T. et al. (1994) J. Biol. Chem. 269:30761–30764); Yama/CPP32β (Tewari, M. et al. (1995) Cell 81:801–809); the product of the mouse gene Nedd2 (Kumar, S. et al. (1992) Biochem. Biophys. Res. Commun. 185:1155–1161; Kumar, S. et al. (1994) Genes Dev. 8:1613–1626); the product of the C. elegans gene, ced-3 (Yuan, J. et al. (1993) Cell 75:641–652); the human protein TX (Faucheu, C., et al., (1995) EMBO J. 14:1914–1922); $ICE_{rel}II$ and $ICE_{rel}III$ (Munday, N. A. et al. (1995) J. Biol. Chem. 270:15870–15876).

The term "interleukin-1β converting enzyme (ICE)" is intended to refer to a protease having an amino acid sequence as disclosed in Cerretti, D. P. et al. (1992) Science 256:97–100 (human) or Nett, M. A. et al. (1992) J. Immunol. 149:3254–3259 (mouse), and other mammalian homologues thereof.

The term "ICE inhibitor" is intended to include chemical agents that inhibit the proteolytic activity of ICE. Examples of ICE inhibitors are known in the art, including, for example, agents disclosed in U.S. Pat. No. 5,411,985, U.S. Pat. No. 5,430,128, U.S. Pat. No. 5,434,248, U.S. Pat. No. 5,565,430, U.S. Pat. No. 5,416,013, PCT Publication WO 94/00154, PCT Publication WO 93/16710, PCT Publication WO 93/14777, PCT Publication WO 93/05071, PCT Publication WO 95/35308, European Patent Application EP 547 699, European Patent Application EP 519 748, U.S. application Ser. No. 08/700,716, now U.S. Pat. No. 5,744,451, and U.S. Provisional applications Ser. Nos. 60/028,322, 60/028,324, 60/028,313 and 60/028,323.

Preferred ICE inhibitors include sulfonamide substituted aspartic acid compounds having the Formula I

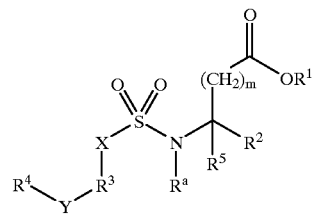

wherein
$R^1$ is hydrogen, $C_1$–$C_6$alkyl, or benzyl;
$R^2$ is —CHO, —CORA, or —CN;
each $R^a$ is independently hydrogen or $C_1$–$C_6$alkyl;
X is a bond, $CH_2$, $CHR^5$, NH, $NR^5$, or O;
$R^3$ is aryl, substituted-aryl, heteroaryl, substituted-heteroaryl, cycloalkyl, substituted-cycloalkyl, heterocycle, or substituted-heterocycle;
Y is absent, $NR^5$, CO, S, O, $SO_2$, —O$(CHR^5)_n$—, $CHR5$, $NR^5CO$, $NC(O)R^5$, $CONR^5$, $OCHR^5$, $CHR^5O$, $SCHR^5$, $CHR^5S$, $SO_2NR^5$, $C_1$–$C_6$alkyl, $NR^5SO_2$, $CH_2CHR^5$, $CHR^5CH_2$, $COCH_2$, or $CH_2CO$;

$R^4$ is absent, aryl, substituted-aryl, $C_1$–$C_8$alkyl, heteroaryl, substituted-heteroaryl, cycloalkyl, $C_1$–$C_6$alkyl, substituted-cycloalkyl, heterocycloalkyl, or substituted-heterocycloalkyl;

each $R^5$ is independently hydrogen, $C_1$–$C_6$alkyl, aryl, —$(CH_2)_n$aryl, or —$(CH_2)_n$cycloalkyl;

each n is independently 0 to 5, m is 1 or 2, and the pharmaceutically acceptable salts, esters, amides, and prodrugs thereof.

In one embodiment of the invention, $R^2$ is CHO.

In another embodiment of the invention, $R^1$ is hydrogen.

In another embodiment of the invention, $R^a$ is hydrogen.

In another embodiment of the invention, X is a bond.

In another embodiment of the invention, $R^3$ is phenyl or substituted phenyl.

In another embodiment of the invention, Y is a bond.

In another embodiment of the invention, Y is O.

In another embodiment of the invention, Y is $CH_2$.

In another embodiment of the invention, $R^4$ is phenyl or substituted phenyl.

In another embodiment of the invention, $R^2$ is CHO, $R^a$ is H, $R^1$ is hydrogen, X is a bond, $R^3$ and $R^4$ are phenyl or substituted phenyl, and Y is a bond, $CH_2$, or O.

In another embodiment of the invention, m is 1 and $R^5$ is hydrogen. In a preferred embodiment, the present invention provides compounds of Formula II

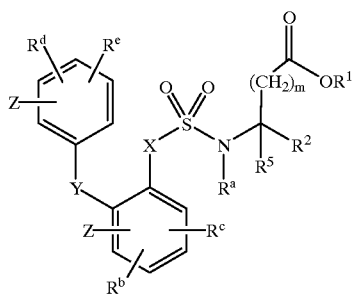

II wherein $R^1$ is hydrogen, $C_1$–$C_6$alkyl, or benzyl;

$R^2$ is —CHO, —CORA, or —CN;

each $R^a$ is independently hydrogen or $C_1$–$C_6$alkyl;

X is a bond, $CH_2$, $CHR^5$, NH, $NR^5$, or O;

Y is a bond, $NR^5$, CO, S, O, $SO_2$, $CHR^5$, $NR^5CO$, $CONR^5$, $OCHR^5$, $CHR^5O$, —$O(CHR^5)_n$—, $SCHR^5$, $CHR^5S$, $SO_2NR^5$, $NR^5SO_2$, $CH_2CHR^5$, $CHR^5CH_2$, $COCH_2$, or $CH_2CO$;

each $R^5$ is independently hydrogen, $C_1$–$C_6$alkyl, aryl, or —$(CH_2)_n$aryl;

each n is independently 0 to 5;

m is 1 or 2;

Each Z is independently hydrogen, or an aryl, substituted aryl, heteroaryl, substituted heteroaryl, cycloalkyl, substituted cycloalkyl, heterocycle, or substituted heterocycle group that is fused to the phenyl group that contains Z as a substituted;

$R^b$, $R^c$, $R^d$, and $R^e$ are each independently hydrogen, $C_1$–$C_6$alkyl, $C_1$–$C_6$alkoxy, —OH, $C_1$–$C_6$ thioalkoxy, halogen, trifluoromethyl, dialkylamino, —$NO_2$, —CN, —$CF_3$, —$CO_2$alkyl, —$SO_3H$, —CHO, —COalkyl, —CONH-alkyl, —$CONHR^q$, —CON(alkyl)$_2$, —$(CH_2)_n$-$NH_2$, —$(CH_2)_n$-NH-alkyl, —$NHR^q$, —$NHCOR^q$, —$(CH_2)_n$OH, —$(CH_2)_nCONH_2$, or —$(CH_2)_nCO_2H$; and $R^q$ is hydrogen or $C_1$–$C_6$alkyl, and the pharmaceutically acceptable salts, esters, amides, and prodrugs thereof.

In another embodiment of the invention with respect to the compounds of Formula II, $R^1$ is hydrogen.

In another embodiment of the invention with respect to the compounds of Formula II, $R^2$ is CHO.

In another embodiment of the invention with respect to the compounds of Formula II, $R^a$ is hydrogen.

In another embodiment of the invention with respect to the compounds of Formula II, X is a bond.

In another embodiment of the invention with respect to the compounds of Formula II, Y is a bond, O, or $CH_2$.

In another embodiment of the invention with respect to the compounds of Formula II, $R^b$ and $R^c$ are hydrogen.

In another embodiment of the invention with respect to the compounds of Formula II, wherein $R^b$, $R^c$, and $R^d$ are hydrogen and $R^e$ is $C_1$–$C_6$ alkyl.

In another preferred embodiment of the invention with respect to the compounds of Formula II, $R^b$ or $R^c$ is located at the para position of the phenyl ring with respect to X and $R^b$ or $R^c$ is —$OCH_3$.

In another embodiment of the invention with respect to the compounds of Formula II, m is 1 and $R^5$ is hydrogen.

In a more preferred embodiment, the present invention provides the compounds 3-(Biphenyl-2-sulfoamino)-4-oxo-butyric acid;

3-(2-Benzyl-benzenesulfonylamino)-4-oxo-butyric acid;

4-Oxo-3-(2-phenoxy-benzenesulfonylamino)-butyric acid;

4-Oxo-3-(2-p-tolyloxy-benzenesulfonylamino)-butyric acid;

3-[2-(4-Isopropyl-phenoxy)-benzenesulfonylamino]-4-oxo-butyric acid;

4-Oxo-3-(2-m-tolyloxy-benzenesulfonylamino)-butyric acid;

3-[2-(3-Isopropyl-phenoxy)-benzenesulfonylamino]-4-oxo-butyric acid; and 3-(4'-Methyl-biphenyl-2-sulfonylamino)-4-oxo-butyric acid.

This invention also includes compounds of the Formula III

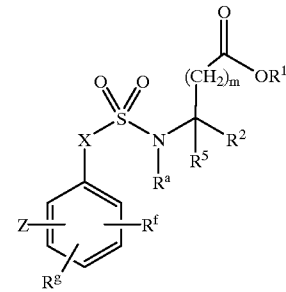

III wherein $R^1$ is hydrogen, $C_1$–$C_6$alkyl, or benzyl;

$R^2$ is —CHO, —CORA, or —CN;

each $R^a$ is independently hydrogen or $C_1$–$C_6$alkyl;

X is a bond, $CH_2$, $CHR^5$, NH, $NR^5$, or O;

$R^5$ is hydrogen, $C_1$–$C_6$alkyl, aryl, or —$(CH_2)_n$aryl;

each n is independently 0 to 5;

m is 1 or 2;

Z is absent, or an aryl, substituted aryl, heteroaryl, substituted heteroaryl, cycloalkyl, substituted cycloalkyl, heterocycle, or substituted heterocycle group that is fused to the phenyl group that contains Z as a substituent;

$R^f$, $R^g$, are each independently hydrogen, $C_1$–$C_6$alkyl, hydroxy, halogen, trifluoromethyl, dialkylamino, —$NO_2$, —CN, —$CO_2H$, —$CO_2$alkyl, —$SO_3H$, —CHO, —COalkyl, —CONH$_2$, —CONH(CH$_2$)$_n$aryl, —CONH(CH$_2$)$_n$-substituted-aryl, —CONH-alkyl, —CONHR$^q$, —CON(alkyl)$_2$, —(CH$_2$)$_n$-NH$_2$, —(CH$_2$)$_n$-NH-alkyl, —NHR$^q$, —NHCOR$^q$, —OR$^q$, —SR$^q$, or —(CH$_2$)$_n$aryl; and R$^q$ is hydrogen or C$_1$–C$_8$alkyl, and the pharmaceutically acceptable salts, esters, amides, and prodrugs thereof.

In a preferred embodiment of the compounds of Formula III, R$^f$ is ortho to X on the phenyl ring, and R$^g$ is hydrogen.

In a preferred embodiment of the compounds of Formula III, Z is hydrogen, m is 1, R$^5$ is hydrogen, and R$^a$ is hydrogen.

In a preferred embodiment of the compounds of Formula III, the present invention provides the compound 3-benzenesulfonylamino-4-oxo-butyric acid.

In general, the groups X and Y in Formulas I, II, and III are spacers for the groups attached to X and Y. It is also noted that certain compounds of Formulas I, II, and III can exist in different, interconvertible forms. An example is shown below when R$^1$ is hydrogen and R$^2$ is CHO.

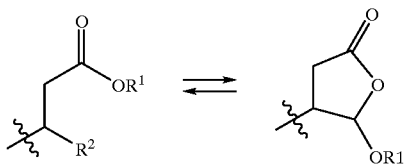

Both the cyclic and acyclic forms are contemplated and are considered part of the present invention. Moreover, it is preferred that the groups attached to R$^3$ be attached at adjacent atoms of R$^3$. For example, if R$^3$ is phenyl, X and Y would have a 1, 2 relationship on R$^3$.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The term "aryl" means an aromatic hydrocarbon. Representative examples of aryl groups include phenyl and naphthyl.

The term "heteroatom" includes oxygen, nitrogen, sulfur, and phosphorus.

The term "heteroaryl" means an aryl group wherein one or more carbon atom of the aromatic hydrocarbon has been replaced with a heteroatom. Examples of heteroaryl groups include furan, thiophene, pyrrole, thiazole, pyridine, pyrimidine, pyrazine, benzofuran, indole, coumarin, quinoline, isoquinoline, and naphthyridine.

The term "cycloalkyl" means a cyclic alkyl group. Examples of cycloalkyl groups include cyclopropane, cyclobutane, cyclopentane, and cyclohexane.

The term "heterocycle" means a cycloalkyl group on which one or more carbon atom has been replaced with a heteroatom. Examples of heterocycles include piperazine, morpholine, and piperidine.

The aryl, heteroaryl, or cycloalkyl groups may be substituted with one or more substituents, which can be the same or different. Examples of suitable substituents include alkyl, alkoxy, thioalkoxy, hydroxy, halogen, trifluoromethyl, amino, alkylamino, dialkylamino, —NO$_2$, —CN, —CO$_2$H, —CO$_2$alkyl, —SO$_3$H, —CHO, —COalkyl, —CONH$_2$, —CONH-alkyl, —CONHR$^q$, —CON(alkyl)$_2$, —(CH$_2$)$_n$-NH$_2$, —OH, —CF$_3$, —OC$_1$-C$_6$alkyl, —(CH$_2$)$_n$-NH-alkyl, —NHR$^q$, —NHCOR$^q$, phenyl, —(CH$_2$)$_n$OH, -(CH$_2$)$_n$C(O)NH$_2$, or —(CH$_2$)$_n$CO$_2$H, where n is 1 to 5 and R$^q$ is hydrogen or alkyl.

The symbol "—" means a bond.

The compounds of Formula I, II, and III can be administered to a patient either alone or as part of a pharmaceutically acceptable composition. The compositions can be administered to patients such as humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents or vehicles, include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar, as well as, high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofuryl alcohol, polyethyleneglycols, and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures, but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 1,000 mg per day. For a normal human adult having a body weight of about 70 kg, a dosage in the range of about 0.01 to about 100 mg per kilogram of body weight per day is preferable. The specific dosage used, however, can vary. For example, the dosage can depend on a numbers of factors including the requirements of the patient, the severity of the condition being treated, and the pharmacological activity of the compound being used. The determination of optimum dosages for a particular patient is well known to those skilled in the art.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic and tautomeric forms, where possible, of the compounds of the invention. The term "salts" refers to the relatively nontoxic, inorganic, and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laureate, borate, benzoate, lactate, phosphate, tosylate, citrate, maleate, flumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as nontoxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Berge, S. M, et al., "Pharmaceutical Salts", *J. Pharm. Sci.*, 1977;66:1–19 which is incorporated herein by reference).

Examples of pharmaceutically acceptable, nontoxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, nontoxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines, and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design,* ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisomeric forms by virtue of the presence of asymmetric centers in the compounds; i.e., each asymmetric carbon can have either the R or S configuration. It is contemplated that all stereoisomeric forms of the compounds as well as mixtures thereof, including racemic mixtures, form part of this invention.

The compounds of the present invention are administered to a patient in need of ICE inhibition. In general, patients in need of ICE inhibition are those patients having a disease or condition in which ICE plays a role. Examples of such diseases include, but are not limited to, inflammatory diseases such as rheumatoid arthritis and inflammatory bowel disease and neuroinflammatory disorders such as stroke. Other diseases include reperfusion injury, Alzheimer's disease, and shigellosis.

A "therapeutically effective amount" is an amount of a compound of Formula I, II, or III that when administered to a patient having a disease that can be treated with a compound of Formula I ameliorates a symptom of the disease. A therapeutically effective amount of a compound of Formula I, II, or III is readily determined by one skilled in the art by administering a compound of Formula I, II, or III to a patient and observing the results.

The following examples illustrate particular embodiments of the invention and are not intended to limit the scope of the specification and claims in any manner.

The compounds of the present invention can be made generally as follows.

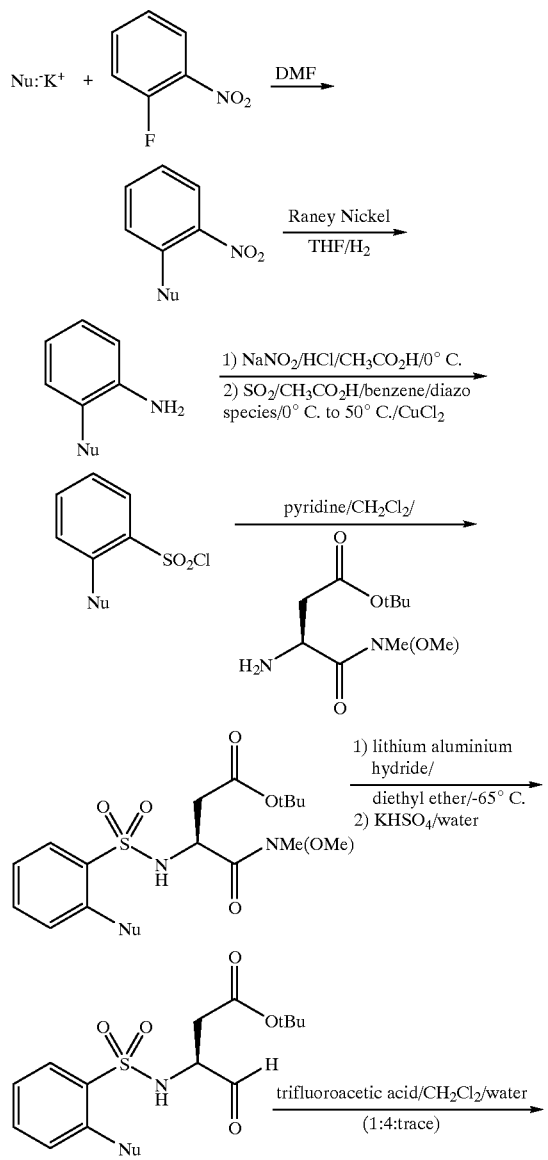

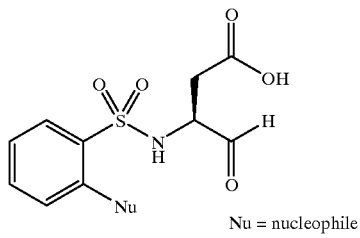

Nu = nucleophile

The term "phosphodiesterase IV inhibitor" is intended to refer to agents that inhibit the activity of the enzyme phosphodiesterase IV. Examples of phosphodiesterase IV inhibitors are known in the art and include 4-arylpyrrolidinones, such as rolipram (see e.g., Sekut, L. et al. (1995) Clin. Exp. Immunol. 100:126–132), nitraquazone (see e.g., Van Wauwe, J. et al. (1995) Inflamm. Res. 44:400–405), denbufylline, tibenelast (see e.g., Banner, K. H. et al. (1996) Br. J. Pharmacol. 119:1255–1261),CP-80633 (see e.g., Cohan, V. L. et al. (1996) J. Pharmacol. Exp. Therap. 278:1356–1361) and quinazolinediones, such as CP-77059 (see e.g., Sekut, L. et al. (1995) Clin. Exp. Immunol. 100:126–132).

The term "beta-2 agonist" is intended to refer to agents that stimulate the beta-2 adrenergic receptor. Examples of beta-2 agonists are known in the art and include salmeterol (see e.g., Sekut, L. et al. (1995) Clin. Exp. Immunol. 99:461–466), fenoterol and isoproterenol (see e.g., Severn, A. et al. (1992) J. Immunol. 148:3441–3445).

The term "STAT4" is intended to refer to a transcription factor involved in IL-12 responses (see e.g., Thierfelder, W. E. et al. (1996) Nature 382:171–174; Kaplan, M. H. et al. (1996) Nature 382:174–177). The term "STAT4 inhibitor" refers to an agent that inhibits the activity of the STAT4 transcription factor such that responses to IL-12 are inhibited.

The term "antibody" as used herein refers to immunoglobulin molecules and immunologically active determinants of immunoglobulin molecules, i.e., molecules that contain an antigen binding site which specifically binds (immunoreacts with) an antigen. The term "antibody" is further intended to include bispecific and chimeric molecules having at least one antigen binding determinant derived from an antibody molecule. Furthermore, although the H and L chains of an Fv fragment are encoded by separate genes, a synthetic linker can be made that enables them to be made as a single protein chain (known as single chain antibody, sAb; Bird et al 1988 Science 242:423–426; and Huston et al. 1988 PNAS 85:5879–5883) by recombinant methods. Such single chain antibodies are also encompassed within the term "antibody", and may be utilized as binding determinants in the design and engineering of a multispecific binding molecule.

The term "antibody fragment" as used herein refers to an active fragment of an antibody that retains the ability to bind (immunoreact with) an antigen. Examples of antibody fragments include: a Fab fragment consisting of the $V_L$, $V_H$, $C_L$ and $C_{H1}$ domains; an Fd fragment consisting of the $V_H$ and $C_{H1}$ domains; an Fv fragment consisting of the $V_L$ and $V_H$ domains of a single arm of an antibody; a dAb fragment (Ward et al, 1989 Nature 341:544–546 ) consisting of a $V_H$ domain; an isolated complementarity determining region (CDR); and an F(ab')$_2$ fragment, a bivalent fragment comprising two Fab' fragments linked by a disulfide bridge at the hinge region. These antibody fragments are obtained using conventional techniques well-known to those with skill in the art, and the fragments are screened for utility in the same manner as are intact antibodies.

The term "engineered binding protein" as used herein is intended to include molecules derived from an antibody or other binding molecule (e.g., a receptor or ligand) that retain a desired binding specificity but that have been engineered by recombinant DNA techniques and/or are expressed using recombinant DNA techniques. Examples of engineered binding proteins include soluble and truncated forms of receptors, dimers of receptors (e.g., p40 IL-12 receptor dimers), and modified or mutated forms of antibodies, ligands or receptors selected using combinatorial libraries (e.g., phage display library techniques).

The terms "steroid resistant disease" and "steroid resistant subject" as used herein are intended to refer to diseases and subjects that do not respond significantly to corticosteroid therapy prior to treatment in accordance with the methods of the invention. Steroid resistance is also referred to as steroid refractoriness.

The term "immunoinflammatory disease or disorder" is intended to include inflammatory diseases and disorders in which immune cells and/or cytokines are involved in the pathophysiology of the disease or disorder. The term "acute inflammatory disorder" is intended to include disorders, and episodes of disorders, characterized by rapid onset of symptoms associated with an inflammatory response and relatively short duration of symptoms, whereas a "chronic inflammatory disorder" is intended to include disorders characterized by the continued presence of symptoms associated with an inflammatory response and ongoing duration of symptoms.

I. Methods of the Invention

In one embodiment, the invention provides a method for modulating responsiveness to a corticosteroid in a subject, comprising administering to the subject:

an agent which antagonizes a factor that regulates production of interferon-γ (IFN-γ) in the subject, the agent being administered at a dosage and by a route sufficient to inhibit production of IFN-γ in the subject; and a corticosteroid, such that responsiveness of the subject to the corticosteroid is modulated as compared to when a corticosteroid alone is administered to the subject.

In one embodiment, the method involves administration of an agent that is an IGIF antagonist. The IGIF antagonist is administered to the subject at a dosage and by a route sufficient to inhibit IGIF activity in the subject. The IGIF antagonist can act, for example, by inhibiting IGIF synthesis in the subject, by inhibiting IGIF cytokine activity in the subject, by inhibiting interaction of IGIF with an IGIF receptor or by inhibiting the activity of an IGIF receptor.

In a preferred embodiment, the IGIF antagonist is an inhibitor of a caspase family protease. Caspase family proteases, and in particular ICE, process the precursor form of IGIF to the mature (i.e., active) form (see e.g., Example 4). Accordingly, although not intending to be limited by mechanism, a caspase family protease inhibitor is thought to antagonize IGIF activity by inhibiting the processing of IGIF from its precursor form to its mature (i.e., active) form.. A preferred caspase family protease inhibitor for use in the methods of the invention is an ICE inhibitor. Additionally or alternatively, other caspase family proteases that are capable of cleaving precursor IGIF to mature IGIF (such as Ich-2 (caspase-4) and $ICE_{rel}III$ (caspase-5)), can be inhibited. Chemical agents that can inhibit the activity of ICE and other caspase family proteases are known in the art, including peptidyl derivatives, azaaspartic acid analogs and gamma-pyrone-3-acetic acid (see e.g., U.S. Pat. No. 5,411, 985, U.S. Pat. No. 5,430,128, U.S. Pat. No. 5,434,248, U.S. Patent No. 5,565,430, U.S. Pat. No. 5,416,013, PCT Publication WO 94/00154, PCT Publication WO 93/16710, PCT Publication WO 93/14777, PCT Publication WO 93/05071, PCT Publication WO 95/35308, European Patent Application EP 547 699 and European Patent Application EP 519 748). Additional suitable inhibitors of ICE and other caspase family inhibitors are disclosed in U.S. Application Serial No. 08/700,716 and U.S. Provisional applications Ser. Nos. 60/028,322, 60/028,324, 60/028,313 and 60/028,323. The exact dosage and regimen for administering an inhibitor of ICE or an ICE-family protease will necessarily depend upon the needs of the subject being treated, the type of treatment, the efficacy of the compound and the degree of disease severity in the subject. However, a nonlimiting example of a dosage range for an inhibitor of ICE and other caspase family proteases is from about 0.05 to about 150 mg/kg body weight/day.

In other embodiments, the IGIF antagonist is an antibody, antibody fragment, or engineered binding protein that binds IGIF or an IGIF receptor. Such binding agents can be prepared by standard methods known in the art for making poly- and monoclonal antibodies and recombinant binding proteins.

In another embodiment, the method of the invention involves administration of an agent that is an IL-12 antagonist. The IL-12 antagonist is administered to the subject at a dosage and by a route sufficient to inhibit IL-12 activity in the subject. The IL-12 antagonist can act, for example, by inhibiting IL-12 synthesis in the subject, by inhibiting IL-12 cytokine activity in the subject, by inhibiting interaction of IL-12 with an IL-12 receptor or by inhibiting the activity of an IL-12 receptor.

In one embodiment, the IL-12 antagonist is an antibody, antibody fragment, or engineered binding protein that binds IL-12 or IL-12 receptor. A preferred IL-12 antagonist is an anti-IL-12 monoclonal antibody. Such antibodies have been described in the art (see e.g., Chizzonite, R, et al. (1991) *J. Immunol.* 147:1548–1556). The ability of anti-IL-12 monoclonal antibodies to inhibit disease responses also has been described in the art (see e.g., Leonard, J. P. et al. (1995) *J. Exp. Med.* 181 :381–386; Neurath, M. F. et al. (1995)*J. Exp. Med.* 182:1281–1290). Another type of IL-12 antagonist is a p40 homodimer (see e.g., Gillessen, S. et al. (1995) *Eur. J. Immunol.* 25:200–206; Gately, M. K. et al. (1996) *Ann. NY Acad. Sci.* 795:1–12; Ling, P. et al. (19905) *J. Immunol.* 154:116–127). Yet another type of IL-12 antagonist is a low affinity form of an IL-12 receptor, as described in European Patent Application EP 638 644 and U.S. Pat. No. 5,536,657.

Nonlimiting examples of IL-12 antagonists for use in the methods of the invention include mono- and polyclonal antibodies and fragments thereof, chimeric antibodies and fragments thereof, soluble IL-12 receptors and fragments thereof, reactive peptides or fragments thereof, chemically or genetically modified peptides of IL-12, subunits of IL-12 and fragments thereof, homopolymers of IL-12 subunits and fragments thereof, and small organic molecules designed to inhibit the bioactivity of IL-12 or IL-1 2 receptors. The preparation of IL-12 antagonists, including: (i) species that bind IL-12 or biologically active fragments thereof, and (ii) species that interfere with the binding of IL-12 to receptors or other binding proteins, have been described in the art (see e.g., PCT Publication WO 95/24918 by Leonard et al., the contents of which are expressly incorporated herein by reference; see also Presky, D. H et al. (1995) *Res. Immunol.* 146:439–445).

In another embodiment, an IL-12 antagonist used in the method of the invention is an agent that stimulates cyclic AMP (cAMP) production in cells that produce IL-12. Production of IL-12 has been shown to be inhibited by increased intracellular production of cAMP (see e.g., van der Pouw Kraan et al. (1995) *J. Exp. Med.* 181:775–779). Examples of agents that can be used to stimulate intracellular cAMP production include phosphodiesterase IV inhibitors and beta-2 agonist. As demonstrated in Example 3, administration of a phosphodiesterase IV inhibitor in a septic shock model inhibits LPS-induced IL-12 production. Examples of suitable phosphodiesterase IV inhibitors for use in the methods of the invention include rolipram, denbufylline, tibenelast, nitraquazone and CP-80633. Examples of beta-2 agonists for use in the methods of the invention include salmeterol, fenoterol and isoproterenol. The exact dosage and regimen for administering a phosphodiesterase IV inhibitor or a beta-2 agonist will necessarily depend upon the needs of the subject being treated, the type of treatment, the efficacy of the compound and the degree of disease severity in the subject. However, a nonlimiting example of a dosage range for phosphodiesterase IV inhibitors or beta-2 agonists is from about 0.05 to about 150 mg/kg body weight/day. In a preferred embodiment, an agent that stimulates cyclic AMP (cAMP) production (e.g., a phosphodiesterase IV inhibitor or a beta-2 agonist) is administered systemically (e.g., orally or intravenously) to inhibit production of IL-12 systemically by monocytes and macrophages.

In another embodiment, an IL-12 antagonist used in the method of the invention is a STAT4 inhibitor. STAT4 is a transcription factor that has been shown to be involved in IL-12 responses (see e.g, Thierfelder, W. E. et al. (1996) *Nature* 382:171–174; Kaplan, M. H. et al. (1996) *Nature* 382:174–177). Accordingly, IL-12 responses in a subject can be inhibited through administration of a STAT4 inhibitor.

Other inhibitors of IL-12 activity that are known in the art also can be used in the methods of the invention. For example, PCT Publication WO 96/40093 discloses biphenyl derivatives for antagonizing IL-12 induced immune responses. Such biphenyl derivatives can be used as IL-12 antagonists in the methods of the invention.

In the methods of the invention, an agent which antagonizes a factor that regulates production of interferon-γ (IFN-γ) is administered to a subject in combination with one or more corticosteroids. The term "in combination with" a corticosteroid is intended to include simultaneous administration of the agent and the corticosteroid, administration of the agent first, followed by the corticosteroid and administration of the corticosteroid first, followed by the agent. Any of the therapeutically useful corticosteroids known in the art can be used in the methods of the invention. Corticosteroids are typically classified by the duration of their tissue effects: short acting compounds (e.g., beclomethasone, flunisolide, hydrocortisone, cortisone), intermediate acting compounds (e.g., prednisone, prednisolone, methylprednisolone, triamcinolone, deflazacort) and long-acting compounds (e.g., dexamethasone, beta methasone). One or more corticosteroids can be administered to the subject by a route and at a dosage effective to achieve the desired therapeutic results. Examples of suitable routes of delivery include intravenous administration, oral administration, topical administration, administration by inhalation (e.g., bronchial administration), and local injection (e.g., intra-joint). The exact dosage and regimen for administering a corticosteroid to the subject will necessarily depend upon the needs of the subject being treated, the type of treatment, the efficacy of the compound and the degree of disease severity in the subject. However, a nonlimiting example of a dosage range for corticosteroids is from about 0.05 mg/day to about 1 gm/day, depending upon the particular corticosteroid used. Certain preferred dosage regimens utilize alternate day administration (e.g., high dose intravenous pulse therapy).

Corticosteroid formulations suitable for administration are well known in the art and commercially available. For example, dexamethasone acetate, 16 mg/ml aqueous suspension, is suitable for intramuscular injection in the treatment of rheumatoid, dermatological, ophthalmic, gastrointestinal, hematologic, neoplastic, allergic conditions and collagen disorders. Nonlimiting examples of dosages include 0.8 mg, 1.6 mg, 4 mg and 16 mg of dexamethasone per injection.

Hydroxycortisone is available as a sterile aqueous solution for intravenous, intramuscular, and subcutaneous injection and is a potent anti-inflammatory agent for conditions such as osteoarthritis, rheumatoid arthritis, juvenile rheumatoid arthritis, acute and chronic bursitis. The preferred initial dosages can be from 15 mg to 250 mg per human subject per day. Preferred dosages are oral or parenteral, and can be administered in half the daily dosage, administered twice per day, or other multiples. Hydrocortisone injection can be added to sodium chloride injection or dextrose injection and administered by intravenous drip. Hydrocortisone valerate, 0.2% by weight, is formulated as a cream for topical use under the name Westcort. Preferred dosages comprise application to affected areas several times daily as thin films.

Beconase (beclomethasone) is available for inflammation of the nasal passages and sinuses, for example, as 8.4 mg for 200 metered spray doses in a 0.042% aqueous suspension, delivered in metered doses of 100 mg containing 42 μg per metered dose, such that daily nasal delivery consists of preferably 42 μg per nostril, 84 μg per nostril, 168 μg per nostril, 336 μg per nostril, 672 μg per nostril, or 1,344 μg per nostril. It is preferably delivered, for example, in an aqueous medium in suspension with microcrystalline cellulose, carboxymethylcellulose sodium, dextrose, benzalkonium chloride, polysorbate 80, and 0.25% v/w phenylethyl alcohol. Additional propellants and media are included in some formulations.

In certain embodiments in which an agent of the invention is coadministered with a corticosteroid, the agent is administered systemically to regulate IFN-γ production systemically while the corticosteroid is administered either locally or systemically. For example, in certain embodiments when a phosphodiesterase IV inhibitor or a beta-2 agonist is administered together with a corticosteroid, the phosphodiesterase IV inhibitor or beta-2 agonist is administered systemically, such as intravenously or orally, and the corticosteroid is administered either systemically or locally. Additionally, in certain embodiments of the methods of the invention, use of a phosphodiesterase IV inhibitor or a beta-2 agonist in combination with a corticosteroid for the treatment of asthma is specifically excluded from the scope of the invention.

The methods of the invention can be used in the treatment of a variety of inflammatory and immunological disorders. For example, in a preferred embodiment, the subject to be treated is suffering from septic shock (i.e., the methods of the invention allow for corticosteroids to be used in the treatment of septic shock). In another preferred embodiment, the subject to be treated is suffering from Crohn's disease. In yet another preferred embodiment, the subject to be treated is suffering from asthma. In still another preferred embodiment, the subject to be treated is suffering from graft-versus-host disease or transplant rejection. In still another preferred embodiment, the subject to be treated is suffering from an autoimmune disease.

In another embodiment, the subject to be treated is suffering from an immunoinflammatory disease or disorder. Non-limiting examples of immunoinflammatory diseases and disorders that may be treated according to the invention include asthma, adult respiratory distress syndrome, systemic lupus erythematosus, inflammatory bowel disease (including Crohn's disease and ulcerative colitis), multiple sclerosis, insulin-dependent diabetes mellitus, autoimmune arthritis (including rheumatoid arthritis, juvenile rheumatoid arthritis, psoriatic arthritis), inflammatory pulmonary syndrome, pemphigus vulgaris, idiopathic thrombocytopenic purpura, autoimmune meningitis, myasthenia gravis, autoimmune thyroiditis, dermatitis (including atopic dermatitis and eczematous dermatitis), psoriasis, Sjögren's Syndrome (including keratoconjunctivitis sicca secondary to Sjögren's Syndrome), alopecia areata, allergic responses due to arthropod bite reactions, aphthous ulcer, iritis, conjunctivitis, keratoconjunctivitis, cutaneous lupus erythematosus, scleroderma, vaginitis, proctitis, drug eruptions (such as Stevens-Johnson syndrome), leprosy reversal reactions, erythema nodosum leprosum, autoimmune uveitis, allergic encephalomyelitis, aplastic anemia, pure red cell anemia, idiopathic thrombocytopenia, polychondritis, Wegener's granulomatosis, chronic active hepatitis, Graves ophthalmopathy, primary biliary cirrhosis, uveitis posterior and interstitial lung fibrosis.

In another embodiment, the subject to be treated is suffering from an acute inflammatory disorder. Examples of acute inflammatory disorders including graft versus host disease, transplant rejection, septic shock, endotoxemia, Lyme arthritis, infectious meningitis (e.g., viral, bacterial, Lyme disease-associated), an acute episode of asthma and acute episodes of an autoimmune disease.

In yet another embodiment, the subject to be treated is suffering from a chronic inflammatory disorder. Nonlimiting examples of chronic inflammatory disorder which can be treated include asthma, rubella arthritis, and chronic autoimmune diseases, such as systemic lupus erythematosus, psoriasis, inflammatory bowel disease, including Crohn's disease and ulcerative colitis, multiple sclerosis and rheumatoid arthritis.

In certain cases, agents that antagonize a particular factor that regulates IFN-γ in the subject may be preferred for the treatment of a particular disorder. For example, although not intending to be limited by mechanism, disorders in which IFN-γ is preferentially or predominantly produced by NK cells preferably are treated using an agent that antagonizes IGIF (such as an ICE inhibitor), in combination with a corticosteroid. Alternatively, disorders in which IFN-γ is preferentially or predominantly produced by T cells preferably are treated using an agent that antagonizes IL-12 (e.g., an anti-IL-12 antibody or an agent that stimulates intracellular production of cAMP), in combination with a corticosteroid. In other circumstances, it may be beneficial to use both an IGIF antagonist and an IL-12 antagonist (e.g., in the treatment of disorders in which IFN-γ production is contributed by both T cells and NK cells).

The agent and the corticosteroid are administered to the subject in need of treatment according to standard routes of drug delivery well known in the art, the particular route and dosage of the agent and the corticosteroid being selected depending upon the needs of the subject being treated, the type of treatment, the efficacy of the compound and the degree of disease severity in the subject. The agent and the corticosteroid are administered at an "effective therapeutic dose", which means that amount of the therapeutic composition which, when administered to a subject produces an amelioration of a disorder in comparison to those subjects which have not been administered the drug. One of ordinary skill in the art can determine and prescribe the effective amount of the therapeutic agents and corticosteroid required. The agents and corticosteroids of the invention are administered to subjects in biologically compatible forms suitable for pharmaceutical administration in vivo to produce a desired therapeutic response. By "biologically compatible form suitable for administration in vivo" is meant a form of the drug to be administered in which any toxic effects and side effects are outweighed by the therapeutic effects of the composition. Moreover, an agent of the invention that antagonizes a factor that regulates production of IFN-γ in a subject is administered to the subject at a dosage and by a route sufficient to inhibit IFN-γ production in the subject. Similarly, an IL-12 antagonist or IGIF antagonist of the invention is administered to a subject at a dosage and by a route sufficient to inhibit IL-12 activity or IGIF activity, respectively, in the subject.

Animal models of inflammatory and immunological disorders that are accepted in the art as being models of human disease can be used to evaluate various therapeutic regiments of the invention. For example, the *P. acnes*/LPS model of septic shock described in the Examples can be used to evaluate the efficacy of therapeutic regimens for the treatment of septic shock. Numerous animal models of autoimmune disease are known in the art and can be applied to the methods herein to evaluate the efficacy of therapeutic regimens, nonlimiting examples of which include experimental colitis (see e.g., Neurath, M. F. et al. (1995) *J. Exp. Med.* 182:1281–1290), experimental allergic encephalomyelitis (see e.g., Leonard, J. P. et al. (1995) *J. Exp. Med.* 181:381–386), collagen-induced arthritis (Banerjee, S. et al. (1989) *J. Immunol.* 142:2237–2243) and the human TNFα transgenic model of polyarthritis (see e.g., Keffer, J. et al. *EMBO J* (1991) 10:4025–4031). For therapeutic regimens involving inhibition of ICE activity, ICE deficient mice can be used as a model of complete inhibition of ICE activity. Such ICE –/– mice have been described in the art (see e.g., Li, P., et al. (1995) *Cell* 80:401–411 and PCT Publication No. WO 96/12025).

The methods of the invention are useful for modulating corticosteroid responsiveness in a variety of clinical settings. For example, in one embodiment, the methods of the invention are used to reverse steroid resistance in a subject, as compared to when a corticosteroid alone is administered to the subject. In another embodiment, the methods of the invention are used to increase steroid sensitivity in a subject, as compared to when a corticosteroid alone is administered to the subject. In yet another embodiment, the corticosteroid is administered to a subject according to a schedule that reduces the dosage of the corticosteroid over time and the method ameliorates a steroid rebound effect associated with administration of reduced dosages of the corticosteroid. The ability of the methods of the invention to increase steroid sensitivity (i.e., to have a "steroid sparing effect") may therefore allow for the use of corticosteroid therapy in clinical situations in which such therapy previously has been contraindicated. For example, use of the methods of the invention may allow for corticosteroid therapy in patients that previously could not be treated because of detrimental side effects of corticosteroid therapy, such as young children (e.g., in juvenile rheumatoid arthritis), patients with uncontrolled diabetes and patients with hypertension.

Another aspect of the invention pertains to a method for modulating responsiveness to a corticosteroid in a subject, comprising:

selecting a subject in need of modulation of responsiveness to a corticosteroid; and administering to the subject an agent which antagonizes a factor that regulates production of interferon-γ (IFN-γ) in the subject, the agent being administered at a dosage and by a route sufficient to inhibit production of IFN-γ in the subject, such that responsiveness of the subject to a corticosteroid is modulated as compared to when a corticosteroid alone is administered to the subject.

The subject that is selected for treatment according to the method can be, for example a subject that is resistant to a corticosteroid prior to administration of the agent. Alternatively, the subject that is selected for treatment can be a subject that is responsive to a corticosteroid prior to administration of the agent but that exhibits increased sensitivity to the corticosteroid after administration of the agent. One examples of such a subject is a patients suffering from a steroid dependent disorder, which disorder can be treated with lower doses of corticosteroids when treated in accordance with the methods of the invention. Another example of such a subject is a patient for whom steroid therapy has been contraindicated due to side effects when the corticosteroid is administered alone but who can tolerate a lower dosage of corticosteroid when the corticosteroid is administered in accordance with the methods of the invention. Still further, the subject that is selected for treatment according to the method can be a subject undergoing corticosteroid therapy but in whom corticosteroid therapy is to be stopped, such that administration of the agent ameliorates a steroid rebound effect in the subject. Agents for antagonizing a factor that regulates production of IFN-γ in the subject are as described hereinbefore.

II. Pharmaceutical Compositions

Another aspect of the invention pertains to pharmaceutical compositions for modulating responsiveness to corticosteroids. In one embodiment, the pharmaceutical composition of the invention comprises an agent which antagonizes a factor that regulates production of interferon-γ (IFN-γ) in the subject, a corticosteroid and a pharmaceutically acceptable carrier. As discussed above, the factor that is antagonized can be, for example, IGIF or IL-12 (i.e., the pharmaceutical composition can comprise an IGIF antagonist or an IL-12 antagonist, as described hereinbefore, a corticosteroid and a pharmaceutically acceptable carrier).

In a preferred embodiment, a pharmaceutical composition of the invention comprises an inhibitor of a caspase family protease, a corticosteroid and a pharmaceutically acceptable carrier. Examples of inhibitors of caspase family proteases, and nonlimiting exemplary dosages, are described hereinbefore. In a preferred embodiment, the inhibitor of the caspase family protease is an ICE inhibitor.

In yet another embodiment, a pharmaceutical composition of the invention comprising IL-12 antagonist, a corticosteroid and a pharmaceutically acceptable carrier. Examples of such IL-12 antagonists are described hereinbefore. In a preferred embodiment, the IL-12 antagonist is an anti-IL-12 monoclonal antibody. In another preferred embodiment, the IL-12 antagonist is a phosphodiesterase IV inhibitor. In yet another preferred embodiment, the IL-12 antagonist is a beta-2 agonist.

As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

The pharmaceutical compositions of the invention can be formulated for administration by a particular route of administration, such as oral administration, intravenous administration, ophthalmic administration, and the like.

In a preferred embodiment, a pharmaceutical composition of the invention is formulated for topical administration. Accordingly, an agent which antagonizes a factor that regulates production of interferon-γ (IFN-γ) in the subject, a corticosteroid and a pharmaceutically acceptable carrier can be formulated into a cream, salve, ointment and the like suitable for application to the skin.

In another preferred embodiment, a pharmaceutical composition of the invention is formulated for administration by inhalation. Accordingly, an agent which antagonizes a factor that regulates production of interferon-γ (IFN-γ) in the subject, a corticosteroid and a pharmaceutically acceptable carrier can be formulated into a nasal spray or an inhalant to allow for delivery of the therapeutic agents to the nasal or sinus passages or the lungs (e.g., the bronchial passages) by inhalation.

This invention is further illustrated by the following examples which should not be construed as limiting. The contents of all references and published patents and patent applications cited throughout the application are hereby incorporated by reference.

EXAMPLE 1: Inhibition of ICE Activity in a Septic Shock Model Results in Steroid Responsiveness In this example, the effect of inhibiting ICE activity on steroid responsiveness in septic shock was examined. A model of septic shock was induced in ICE-deficient (ICE −/−) and wild type (ICE +/+) mice, followed by treatment with a corticosteroid. The ICE −/− mice serve as a model of complete inhibition of ICE activity (see Li, P., et al. (1995) *Cell* 80:401–411 for further description of the ICE deficient mice). The responsiveness of the animals to corticosteroid treatment was determined by monitoring the levels of the inflammatory cytokine TNFα in the sera of the mice.

ICE-deficient and wild type mice first were sensitized with *Propionibacterium acnes* cell wall material (1 mg per mouse) to induce low grade inflammation and six days later were challenged with lipopolysaccharide (LPS) (1 μg per mouse in 0.1 ml of saline i.v.). Thirty minutes after LPS administration, the mice were treated with the corticosteroid dexamethasone (4 mg/kg per mouse in 0.5 ml 95% saline/0.5% ethanol, i.p.). Control mice were treated with vehicle alone. All mice were bled 90 minutes after LPS administration and the serum samples were analyzed for the presence of TNFα by standard ELISA.

The results are shown in FIG. 1. Wild type and ICE deficient mice treated with vehicle alone had similar levels of serum TNFα. Treatment of wild type mice with dexamethasone did not significantly affect serum TNFα levels, demonstrating their resistance to steroid treatment in this septic shock model. In contrast, treatment of the ICE deficient mice with dexamethasone suppressed serum TNFα levels by 74% (p<0.002). These data indicate that inhibition of ICE activity reverses resistance to steroid treatment in a septic shock model.

EXAMPLE 2: Inhibition of ICE Activity in a Septic Shock Model Increases Steroid Sensitivity In this example, the effect of inhibiting ICE activity on steroid sensitivity in septic shock was examined. The same LPS/*P. acnes* model of septic shock described in Example 1 was used, except that ICE deficient and wild type mice were pretreated with vehicle or a corticosteroid 15 minutes prior to challenge with LPS. The responsiveness of the animals to corticosteroid treatment again was determined by monitoring the levels of the inflammatory cytokine TNFα in the sera of the mice.

ICE-deficient and wild type mice first were sensitized with *Propionibacterium acnes* cell wall material (1 mg per mouse) to induce low grade inflammation and six days later were challenged with lipopolysaccharide (LPS) (1 μg per mouse in 0.1 ml of saline i.v.). Fifteen minutes prior to LPS challenge, the animals were treated with decreasing amounts of the corticosteroid dexamethasone (0.05, 0.005 or 0.0005 mg/kg per mouse in 0.5 ml 95% saline/0.5% ethanol, i.p.). Control mice were treated with vehicle alone. All mice were bled 90 minutes after LPS administration and the serum samples were analyzed for the presence of TNFα by standard ELISA.

Figure 2:
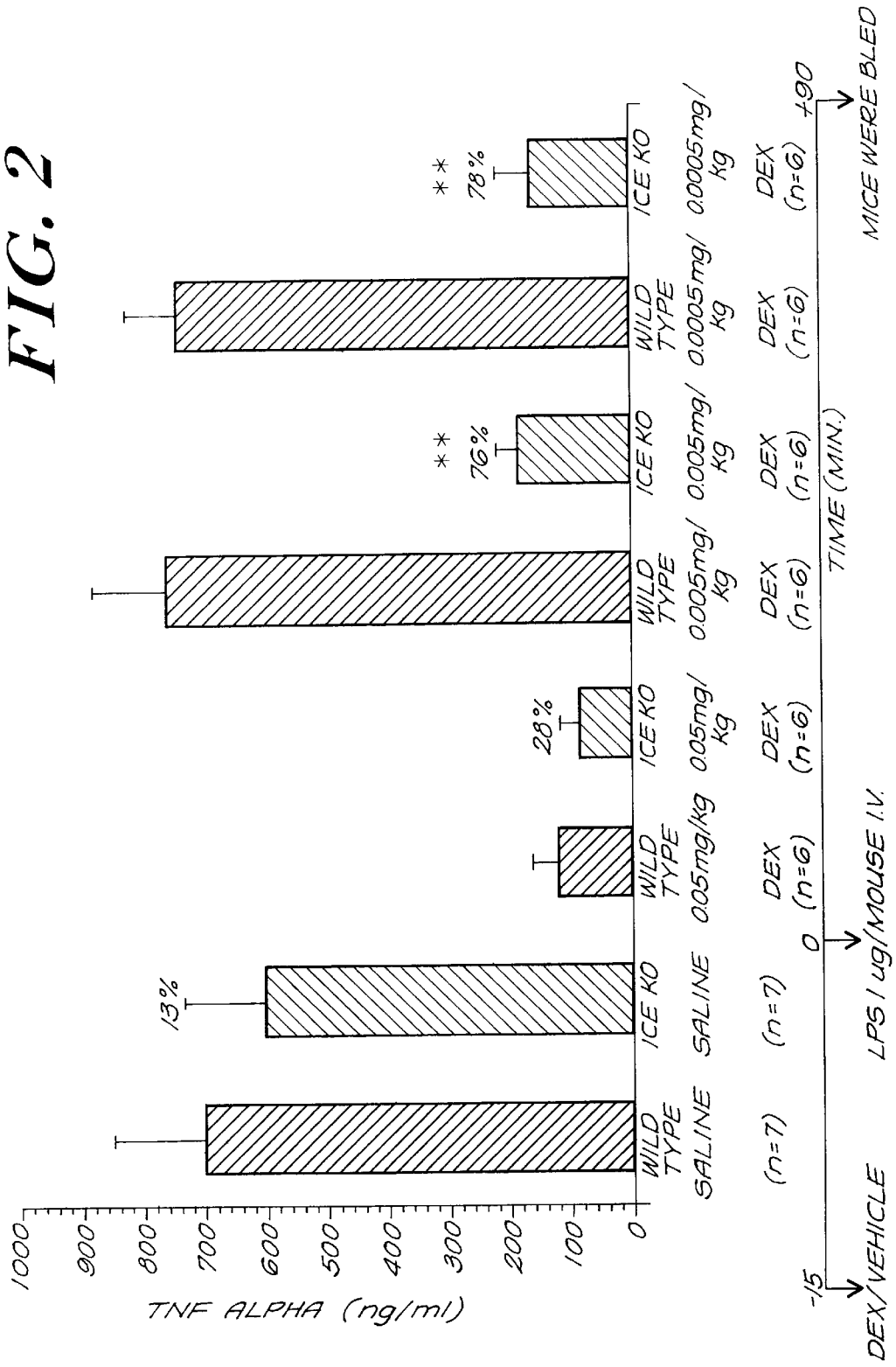
FIG. 2 is a bar graph showing serum TNFα levels (in ng/ml) in wild type (solid bars) and ICE-deficient (hatched bars) mice pretreated with vehicle alone or decreasing amounts of dexamethasone (0.05, 0.005 or 0.0005 mg/kg) in the LPS/P. acnes septic shock model, demonstrating that the ICE-deficient mice maintain steroid responsiveness to decreasing steroid dosages in contrast to the wild type mice.

The results are shown in FIG. 2. Both the wild type and the ICE deficient mice exhibited responsiveness to pretreatment with 0.05 mg/kg of dexamethasone. In contrast, ICE deficient mice pretreated with only 0.005 or 0.0005 mg/kg dexamethasone exhibited 76% and 78% (p<0.005) lower serum TNFα levels, respectively, compared to the lack of TNFα suppression in the wild type animals similarly treated. These data indicate that inhibition of ICE activity results in increased steroid sensitivity in a septic shock model, since 10–100 fold lower doses of dexamethasone were therapeutically effective in the ICE deficient animals as compared to the wild type animals.

EXAMPLE 3: A Phosphodiesterase IV Inhibitor Reduces IL-12 Production

In this example, the effect of a phosphodiesterase IV inhibitor, Rolipram, on LPS-induced IL-12 production was examined. B6 mice were pretreated with vehicle or Rolipram (30 mg/kg in 0.5 ml 0.1% methyl cellulose, i.p.) 15 minutes prior to challenge with LPS (10 μg/mouse, i.v.). Ninety minutes following LPS administration, the mice were bled and serum levels of IL-12 were determined by standard ELISA.

Figure 3:
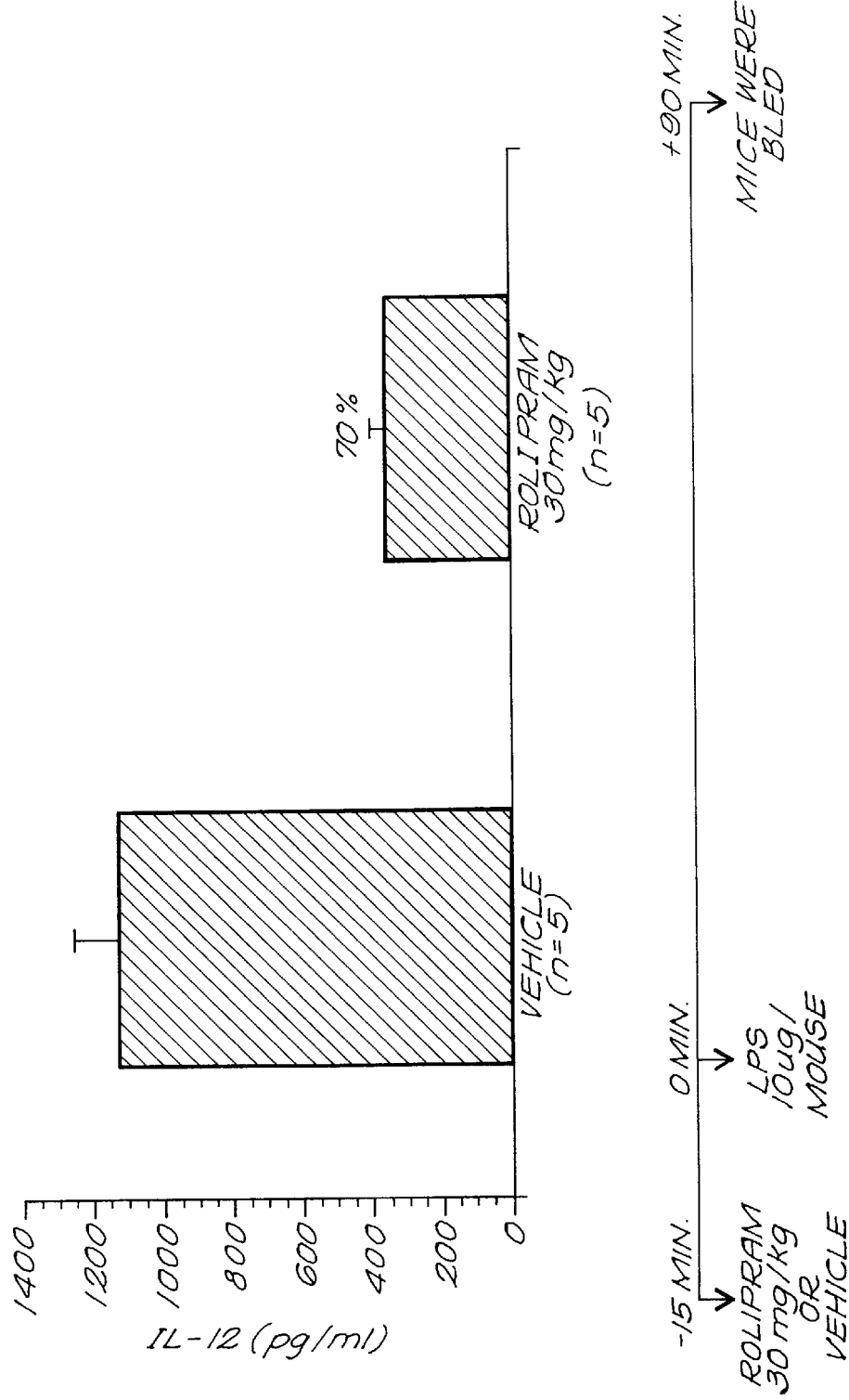
FIG. 3 is a bar graph showing LPS-induced serum IL-12 (in pg/ml) in B6 mice pretreated with vehicle alone or with the phosphodiesterase IV inhibitor, rolipram, demonstrating that treatment with the phosphodiesterase IV inhibitor inhibits production of IL-12.

The results are shown in FIG. 3. Mice pretreated with Rolipram had 70% lower serum IL-12 levels than mice pretreated with vehicle alone. These data indicate that phosphodiesterase IV inhibitors are effective for inhibiting the production of LPS-induced IL-12.

EXAMPLE 4: Cleavage of IGIF by Caspase Family Proteases

The ability of various recombinant (i.e., *E. coli* expressed) caspase family proteases to cleave precursor IGIF (proIGIF) to mature IGIF was tested in an in vitro proteolysis assay. Cleavage of poly(ADP-ribose) polymerase (PARP) was used as a positive control. The results are summarized below in Table 1.

TABLE 1

Proteolysis of proIGIF by Recombinant Caspases

| | | | % Cleavage | |
|---|---|---|---|---|
| Caspase* | | Concentration (μg/ml) | proIGIF | PARP |
| ICE | (1) | 1.25 | 100 | 99 |
| ICH-2 | (4) | 5.00 | 82 | 93 |
| ICE$_{rel}$III | (5) | 20.00 | 55 | 90 |
| CPP32 | (3) | 5.00 | 0$^a$ | 100 |
| Mch2 | (6) | 10.00 | 2 | 96 |
| Mch3 | (7) | 5.00 | 32$^b$ | 97 |
| ICH-1 | (2) | 75.00 | 5 | 98 |

*Caspases are numbered in parenthesis as recommended in Alnemri et al. (1996) Cell 87:171.
$^a$CPP32 (5 μg/ml) cleaved proIGIF but generated a 12 kDa and a 10 kDa fragment instead of the expected 18 kDa fragment.
$^b$Unlike other caspases, the Mch3 precursor expressed in *E. coli* does not undergo autocatalysis to generate an active protease. Addition of ICE was required to initiate Mch3 autocatalysis and generate an active Mch3 protease. Partial cleavage of proIGIF by Mch3 is mediated by the presence of ICE in the Mch3 preparation.

EXAMPLE 5: Treatment of Septic Shock

Patients who present in a clinical setting with septic shock (e.g., in conjunction with infected abrasions, projectile wounds, or systemic bacteremias from other sources) are administered agent selected from an ICE inhibitor, a phosphodiesterase IV inhibitor (e.g., rolipram, 30 mg/kg) and an anti-IL-12 monoclonal antibody, together with a corticosteroid (e.g., high dose methylprednisolone, 1 gm/day, i.v.). The corticosteroid and the agent can be administered simultaneously, or alternatively, the agent can be administered before or after corticosteroid administration. Patients are also treated with appropriate antibiotic therapy.

EXAMPLE 6: Treatment of Transplant Rejection

Patients who are to receive a kidney transplant are administered an agent selected from ICE inhibitor, a phosphodiesterase IV inhibitor (e.g., rolipram, 30 mg/kg) and an anti-IL-12 monoclonal antibody together with a corticosteroid (e.g., oral prednisone, 25–75 mg/day). Treatment preferably is begun prior to receipt of the donated kidney (e.g., drug administration may begin 24 hours prior to receipt of the donated kidney), with dosages to be repeated as needed (e.g., every 12 hours). The corticosteroid and the agent can be administered simultaneously, or alternatively, the agent can be administered before or after corticosteroid administration. Patients are also treated with additional immunosuppressive therapy (such as cyclosporin A treatment or OKT3 antibody treatment) so that immune rejection and inflammatory response are simultaneously suppressed.

EXAMPLE 7: Amelioration of the Steroid Rebound Effect

Patients with asthma, allergic rhinitis inflammation or rheumatoid arthritis who are undergoing treatment with a corticosteroid inhalant or with systemic corticosteroids, and who are to enter a scheduled withdrawal from steroid treatment, are administered an agent selected from an ICE inhibitor, a phosphodiesterase IV inhibitor (e.g., rolipram, 30 mg/kg) and an anti-IL-12 monoclonal antibody. Patients are preferably treated prior to the tapering or discontinuance of steroid treatment to ameliorate the steroid rebound effect that can result from cessation of steroid therapy. As needed, patients can be treated with additional nonsteroidal anti-inflammatory agents.

EXAMPLE 8: Treatment of an Acute Episode of an Autoimmune Disease

Patients suffering from an acute flare-up of an autoimmune disease such as inflammatory bowel disease (e.g., ulcerative colitis or Crohn's disease) are administered an agent selected from ICE inhibitor, a phosphodiesterase IV inhibitor (e.g., rolipram, 30 mg/kg) and an anti-IL-12 monoclonal antibody together with a corticosteroid (e.g., oral prednisone, 25–75 mg/day). The corticosteroid and the agent can be administered simultaneously, or alternatively, the agent can be administered before or after corticosteroid administration. Patients can also be treated with additional immunosuppressive therapy to control the acute flare up of the autoimmune disease.

EXAMPLE 9: Treatment of a Chronic Autoimmune Disease

Patients suffering from chronic autoimmune disease such as Crohn's disease are administered an agent selected from ICE inhibitor, a phosphodiesterase IV inhibitor (e.g., rolipram, 30 mg/kg) and an anti-IL-12 monoclonal antibody together with a corticosteroid (e.g., oral prednisone, 25–75 mg/day). The corticosteroid and the agent can be administered simultaneously, or alternatively, the agent can be administered before or after corticosteroid administration. Patients can also be treated with additional immunosuppressive therapy to control the autoimmune disease.

EXAMPLE 10
3-(Biphenyl-2-sulfoamino)-4-oxo-butyric acid

Biphenyl-2-sulfonyl chloride was obtained using a known procedure (Neale A. J., Rawlings T. J., McCall E. B., Tetrahedron, 1965;21:1299–1313). In general, the sulfonyl chloride (3.2 mmol) was stirred in dichloromethane (20 mL) with pyridine (12 mmol) and Asp(OtBu)-NMe(OMe) [Asp=aspartic acid; tBu=tert-butyl; Me=methyl] (2.9 mmol). After stirring 16 hours at room temperature, dichloromethane was added, and the organic layer was washed sequentially with 10% sulfuric acid, water, and then brine. Removal of the solvent provided the product as a colorless foam. Chromatography on silica gel eluting with 7:3 diethyl ether/hexanes gave product as a colorless foam (750 mg, 56%). The resulting sulfonamide was dissolved diethyl ether and cooled to −65° C. Lithium aluminum hydride (1.5 equivalents) was added to the solution and the reaction temperature was maintained for 2 hours. The excess hydride was quenched by the addition of potassium hydrogen sulfate (2 equivalents) dissolved in water. After warming to room temperature, ether was added and the organic layer was washed with water and then brine. The solvent was evaporated to give crude product as a colorless oil. Chromatography on silica gel (3:2 ether/hexanes) gave the aldehyde (327 mg, 50%). The aldehyde was treated with 3:1 dichloromethane/trifluoroacetic acid (20 mL) containing a trace of water for 2 hours. The solvent was evaporated, excess trifluoroacetic acid was chased with toluene and then ether to give product as a colorless foam (242 mg, 90%). $^1$H NMR (CD$_3$OD) as the lactol 8.05 (m, 1H), 7.60 (t, 1H), 7.53 (t, 1H), 7.41 (m, 5H), 7.30 (d, 1H), 4.42 (s, 1H), 3.63 (s, 1H), 2.50 (m, 1H), 2.30 (m, 1H);

Mass Spectrometry—Chemical Ionization (MS CI)+1% NH$_3$ in CH$_4$ 334 (M+H)$^+$.

EXAMPLE 11

3-Benzenesulfonylamino-4-oxo-butyric acid

Benzenesulfonyl chloride was employed to acylate the amine of Asp(OtBu)-NMe(OMe); from the resulting sulfonamide, final product was obtained as a colorless foam employing the methods previously described in Example 1. $^1$H NMR (CD$_3$OD) as the lactol 7.87 (m, 2H), 7.58 (m, 3H), 4.44, 4.38 (d, 1H), 3.74 (m, 1H), 2.57 (m, 1H), 2.27 (m, 1H); MS CI+1% NH$_3$ in CH$_4$ 240 (M-OH)$^+$.

EXAMPLE 12

3-(2-Benzyl-benzenesulfonylamino)-4-oxo-butyric acid

Diphenylmethane-2-sulfonyl chloride was employed to acylate the amine of Asp(OtBu)-NMe(OMe); from the resulting sulfonamide, final product was obtained as a colorless foam (62 mg, 9%) employing the methods previously described in Example 1. $^1$H NMR (CD$_3$OD) as the lactol 8.00 (dd, 1H), 7.42 (t, 1H), 7.25 (m, 6H), 7.05 (dd, 1H), 4.54, 4.50 (d, 1H), 4.01 (s, 2H), 3.63 (m, 1H), 2.58 (m, 1H), 2.37 (m, 1H); MS CI+1% NH$_3$ in CH$_4$ 304 (M-CHO)$^+$.

EXAMPLE 13

4-Oxo-3-(2-phenoxy-benzenesulfonylamino)-butyric acid

Diphenylether-2-sulfonyl chloride was employed to acylate the amine of Asp(OtBu)-NMe(OMe); from the resulting sulfonamide, final product was obtained as a colorless foam (72 mg, 7%) employing the methods previously described in Example 1. $^1$H NMR (CD$_3$OD) as the lactol 7.95 (d, 1H), 7.43 (m, 3H), 7.20 (m, 4H), 6.82 (d, 1H), 4.58, 4.52 (d, 1H), 3.75 (m, 1H), 2.70–2.40 (m, 2H); MS APCI probe temperature 450° C., cone voltage 25 volts, acetonitrile: methanol 4:1, 350.5 (M+H)$^+$.

EXAMPLE 14

4-Oxo-3-(2-p-tolyloxy-benzenesulfonylamino)-butyric acid (4'-Methylphenyl) phenylether-2-sulfonyl chloride was employed to acylate the amine of Asp(OtBu)-NMe(OMe); from the resulting sulfonamide, final product was obtained as a colorless foam (152 mg, 15%) employing the methods previously described in Example 1. $^1$H NMR (CD$_3$OD) as the lactol 7.90 (d, 1H), 7.48 (d, 1H), 7.35-7.00 (m, 5H), 6.80 (d, 1H), 4.55, 4.50 (d, 1H), 3.75 (m, 1H), 2.70-2.42 (m, 2H), 2.35 (s, 3H); MS APCI probe temperature. 450° C., cone voltage 25 volts, acetonitrile: methanol 4:1, 363.1 (M+H)$^+$.

EXAMPLE 15

3-[2-(4-Isopropyl-phenoxy)-benzenesulfonylamino]-4-oxo-butyric acid (4'-Isopropylphenyl)phenylether-2-sulfonyl chloride was employed to acylate the amine of Asp(OtBu)-NMe(OMe); from the resulting sulfonamide, final product was obtained as a colorless foam (248 mg, 22%) employing the methods previously described in Example 1. $^1$H NMR (CD$_3$OD) as the lactol 7.92 (d, 1H), 7.50 (t, 1H), 7.32 (m, 2H), 7.13 (m, 3H), 6.82 (d, 1H), 4.58, 4.52 (d, 1H), 3.75 (m, 1H), 2.95 (m, 1H), 2.70-2.42 (m, 2H), 1.25 (d, 6H); MS APCI probe temperature 450° C., cone voltage 25 volts, acetonitrile: methanol 4:1, 392.4 (M+H)$^+$.

EXAMPLE 16

4-Oxo-3-(2-m-tolyloxy-benzenesulfonylamino)-butyric acid (3'-Methylphenyl) phenylether-2-sulfonyl chloride was employed to acylate the amine of Asp(OtBu)-NMe(OMe); from the resulting sulfonamide, final product was obtained as a colorless foam (85 mg, 8%) employing the methods previously described in Example 1. $^1$H NMR (CD$_3$OD) as the lactol 7.90 (d, 1H), 7.50 (t, 1H), 7.35-7.13 (m, 2H), 7.10-6.80 (m, 4H), 4.58-4.52 (d, 1H), 3.76 (m, 1H), 2.65-2.42 (m, 2H), 2.35 (s, 3H); MS APCI probe temperature 450° C., cone voltage 25 volts, acetonitrile: methanol 4:1, 363.1 (M+H)$^+$.

EXAMPLE 17

3-[2-(3-Isopropyl-phenoxy)-benzenesulfonylamino]-4-oxo-butyric acid (3'-Isopropylphenyl) phenylether-2-sulfonyl chloride was employed to acylate the amine of Asp(OtBu)-NMe(OMe); from the resulting sulfonamide, final product was obtained as a colorless foam (334 mg, 29%) employing the methods previously described in Example 1. $^1$H NMR (CD$_3$OD) as the lactol 7.90 (d, 1H), 7.50 (t, 1H), 7.45 (m, 1H), 7.25-6.80 (m, 5H), 4.58, 4.52 (d, 1H), 3.78 (m, 1H), 2.90 (m, 1H), 2.70-2.40 (m, 2H), 1.25 (d, 6H); MS APCI probe temperature 450° C., cone voltage 25 volts, acetonitrile: methanol 4:1, 392.5 (M+H)$^+$.

EXAMPLE 18

3-(4'-Methyl-biphenyl-2-sulfonylamino)-4-oxo-butyric acid (4'-Methyl)biphenyl-2-sulfonyl chloride was employed to acylate the amine of Asp(OtBu)-NMe(OMe); from the resulting sulfonamide, final product was obtained as a colorless foam (334 mg, 29%) employing the methods previously described. $^1$H NMR (CD$_3$OD) as the lactol 8.03 (m, 1H), 7.60 (m, 1H), 7.50 (m, 1H), 7.35 (m, 3H), 7.21 (m, 2H), 4.41 (d, 1H), 4.60 (m, 1H), 2.45 (m, 1H), 2.40 (s, 3H), 2.35 (m, 1H); MS APCI probe temperature 450° C., cone voltage 25 volts, acetonitrile: methanol 4:1, 348.5 (M+H)$^+$.

EXAMPLE 19

3-(2-Isobutoxy-benzenesulfonylamino)-4-oxo-butyric acid 2-(Isobutoxy)-benzenesulfonyl chloride was employed to acylate the amine of Asp(OtBu)-NMe(OMe). From the resulting sulfonamide, final product was obtained as a colorless foam (112 mg, 56%) employing methods previously described. $^1$H NMR (CD$_3$OD) as the lactol 7.81 (m, 1H), 7.58 (m, 1H), 7.17 (dd, 1H), 7.05 (m, 1H), 4.50, 4.40 (d, 1H), 3.85 (d, 2H), 3.61 (m, 1H), 2.45 (m, 2H), 2.20 (m, 1H), 1.04 (d, 6H); MS APCI Probe temperature 450° C., cone voltage 25 volts, acetonitrile, 330.5 (M+H)$^+$.

EXAMPLE 20

3-[2-(2-Methyl-pentanoylamino)-benzenesulfonylamino]-4-oxo-butyric acid 2-Nitrobenzenesulfonyl chloride was employed to acylate the amine of Asp(OtBu)-NMe(OMe) employing methods previously described. The resulting nitrosulfonamide was reduced employing 5% Pd on carbon and hydrogen gas to provide the aminosulfonamide $^1$H NMR (CDCl$_3$) 7.70 (d, 1H), 7.30 (t, 1H), 6.76 (m, 2H), 5.92 (d, 1H), 4.60 (m, 1H), 3.63 (s, 3H), 3.02 (s, 3H), 2.62-2.39 (m, 2H), 1.42 (s, 9H); MS CI+1% NH$_3$ in CH$_4$ 332 (M-tBu)$^+$. The aminosulfonamide (400 mg, 1.0 mmol) was acylated employing 2-methylopentanoyl chloride (1.5 mmol) and triethylamine (3 mmol) in dichloromethane (5 mL). Chromatography of the crude reaction product (4:1, diethyl ether, hexane) gave the acylated amine (148 mg, 30%) 1H NMR (CDCl$_3$) 9.34 (d, 1H), 8.55 (dd, 1H), 7.86 (d, 1H), 7.55 (t, 1H), 7.17 (t, 1H), 5.90 (d, 1H), 4.51 (m, 1H), 3.58 (s, 3H), 3.03 (m, 3H), 2.43 (m, 3H), 1.80-1.25 (m, 4H), 1.40 (s, 9H), 1.22 (d, 3H), 0.94 (t, 3H); MS APCI Probe temperature 450° C., cone voltage 25 volts, acetonitrile:methanol 4:1, 486.6 (M+H)$^+$. Final product was obtained from this sulfonamide employing methods previously described. $^1$H NMR (CD$_3$OD) as the lactol 8.30 (m, 1H), 7.93 (m, 1H), 7.64-7.20 (m, 4H), 4.50-4.25 (m, 2H), 3.63 (m, 1H), 2.73-2.20 (m, 3H), 1.65 (m, 1H), 1.42 (m, 2H), 1.22 (d, 3H), 0.97 (t, 3H).

EXAMPLE 21

4-Oxo-3-(2-o-tolyloxy-benzenesulfonylamino)-butyric acid 2-(o-Tolyloxy)-benzenesulfonyl chloride was employed to acylate the amine of Asp(OtBu)-NMe(OMe). From the resulting sulfonamide, final product was obtained as a colorless foam (206 mg, 66%) employing methods previously described. $^1$H NMR (CD$_3$OD) as the lactol; 7.90 (m, 1H), 7.43 (m, 1H), 7.38-7.08 (m, 5H), 6.62 (d, 1H), 4.58 (dd, 1H), 3.79 (m, 1H), 2.70-2.42 (m, 2H), 2.03 (m, 3H); MS APCI Probe temperature 450° C., cone voltage 25 volts, acetonitrile:methanol 4:1, 364.4 (M+H)$^+$.

EXAMPLE 22

4-Oxo-3-(2-phenethyl-benzenesulfonylamino)-butyric acid 2-(Phenethyl)-benzenesulfonyl chloride was employed to acylate the amine of Asp(OtBu)-NMe(OMe). From the resulting sulfonamide, final product was obtained as a colorless foam (56 mg, 25%) employing methods previously described. $^1$H NMR (CD$_3$OD) as the lactol; 8.00 (m, 1H), 7.60-7.10 (m, 8H) 4.50, 4.45 (d, 1H), 3.63 (m, 1H), 3.30 (m, 2H), 2.97 (m, 2H), 2.62-2.42 (m, 2H); MS APCI Probe temperature 450° C., cone voltage 25 volts, acetonitrile:methanol 4:1, 362.5 (M+H)$^+$.

EXAMPLE 23

3-(2-Cyclohexyloxy-benzenesulfonylamino)-4-oxo-butyric acid 2-(Cyclohexyloxy)-benzenesulfonyl chloride was employed to acylate the amine of Asp(OtBu)-NMe(OMe). From the resulting sulfonamide, final product was obtained as a colorless foam (190 mg, 95%) employing methods previously described. $^1$H NMR (CD$_3$OD) as the lactol; 7.80 (m, 1H), 7.57 (m, 10H), 7.23-6.98 (m, 2H), 4.58 (m, 1H), 4.50, 4.40 (d, 1H), 3.63 (m, 1H), 2.45 (m, 2H), 2.10-1.40 (m, 10H); MS APCI Probe temperature 450° C., cone voltage 25 volts, acetonitrile:methanol 4:1, 356.5 (M+H)$^+$.

EXAMPLE 24

3-[2-(1-Chloro-naphthalen-2-yloxy)-benzenesulfonylamino]-4-oxo-butyric acid 2-(1-Chloro-naphthalen-2-yloxy)-benzenesulfonyl chloride was employed to acylate the amine of Asp(OtBu)-NMe(OMe). From the resulting sulfonamide, final product was obtained as a colorless foam (199 mg, 92%) employing methods previously described. $^1$H NMR (CD$_3$OD) as the lactol; 8.30 (d, 1H), 7.93 (m, 3H), 7.70 (m, 1H), 7.60 (m, 1H), 7.48 (m, 1H), 7.39 (m, 1H), 7.20 (m, 1H), 6.75 (d, 1H), 4.63, 4.58 (d, 1H), 3.83 (m, 1H), 2.40 (m, 2H); MS APCI Probe temperature 450° C., cone voltage 25 volts, acetonitrile:methanol 4:1, 434.4 (M+H)$^+$.

EXAMPLE 25

4-Oxo-3-[2-(5,6,7,8-tetrahydro-naphthalen-2-yloxy)-benzenesulfonylamino]-butyric acid 2-(5,6,7,8-tetrahydro-naphthalen-2-yloxy)-benzenesulfonyl chloride was employed to acylate the amine of Asp(OtBu)-NMe(OMe). From the resulting sulfonamide, final product was obtained as a colorless foam (205 mg, 87%) employing methods previously described. $^1$H NMR (CD$_3$OD) as the lactol; 7.90 (m, 1H), 7.42 (m, 1H), 7.17 (m, 2H), 7.00 (d, 2H), 6.90 (m, 1H), 6.62 (d, 2H), 4.58, 4.46 (d, 1H), 3.78 (m, 1H), 2.81 (m, 2H), 2.63 (m, 2H), 2.50 (m, 2H), 1.80 (m, 4H); MS APCI Probe temperature 450° C., cone voltage 25 volts, acetonitrile:methanol 4:1, 404.5 (M+H)$^+$.

EXAMPLE 26

4-Oxo-3-(2-phenethyloxy-benzenesulfonylamino)-butyric acid 2-phenethyloxy-benzenesulfonyl chloride was employed to acylate the amine of Asp(OtBu)-NMe(OMe). From the resulting sulfonamide, final product was obtained as a colorless foam (224 mg, 69%) employing methods previously described. $^1$H NMR (CD$_3$OD) as the lactol; 7.78 (m, 1H), 7.55 (m, 1H), 7.42-7.00 (m, 7H), 4.35 (m, 2H), 4.30, 4.20 (d, 1H), 3.55 (m, 1H), 3.20 (t, 2H), 2.52-2.14 (m, 2H); MS APCI Probe temperature 450° C., cone voltage 25 volts, acetonitrile:methanol 4:1, 378.4 (M+H)$^+$.

EXAMPLE 27

3-[2-(2-Ethyl-phenoxy)-benzenesulfonylamino]-4-oxo-butyric acid 2-(2-Ethyl-phenoxy)-benzenesulfonyl chloride was employed to acylate the amine of Asp(OtBu)-NMe(OMe). From the resulting sulfonamide, final product was obtained as a colorless foam (295 mg, 70%) employing methods previously described. $^1$H NMR (CD$_3$OD) as the lactol; 7.92 (m, 1H), 7.40 (m, 2H), 7.30-7.05 (m, 4H), 6.63 (d, 1H), 4.58, 4.56 (d, 1H), 3.78 (m, 1H), 2.60-2.42 (m, 4H), 1.16 (t, 1H); MS APCI Probe temperature 450° C., cone voltage 25 volts, acetonitrile:methanol 4:1, 378.4 (M+H)$^+$.

EXAMPLE 28

3-[2-(4-sec-Butyl-phenoxy)-benzenesulfonylamino]-4-oxo-butyric acid 2-(4-sec-Butyl-phenoxy)-benzenesulfonyl chloride was employed to acylate the amine of Asp(OtBu)-NMe(OMe). From the resulting sulfonamide, final product was obtained as a colorless foam (295 mg, 70%) employing methods previously described. $^1$H NMR (CD$_3$OD) as the lactol; 7.92 (m, 1H), 7.48 (t, 1H), 7.30-7.07 (m, sH), 6.82 (d, 1H), 4.56, 4.53 (d, 1H), 3.75 (m, 1H), 2.70-2.43 (m, 3H), 1.62 (m, 2H), 1.24 (d, 3H), 0.83 (t, 3H); MS APCI Probe temperature 450° C., cone voltage 25 volts, acetonitrile:methanol 4:1, 406.5 (M+H)$^+$.

EXAMPLE 29

3-[2-(Biphenyl-4-yloxy)-benzenesulfonylamino]-4-oxo-butyric acid 2-(Biphenyl-4-yloxy)-benzenesulfonyl chloride was employed to acylate the amine of Asp(OtBu)-NMe(OMe). From the resulting sulfonamide, final product was obtained as a colorless foam (334 mg, 88%) employing methods previously described. ¹H NMR (CD₃OD) as the lactol; 7.95 (m, 1H), 7.63 (m, 4H), 7.58-7.08 (m, 7HO, 6.94 (d, 1H), 4.59, 4.55 (d, 1H), 3.75 (m, 1H), 2.57 (m, 2H); electrospray MS (50:50 acetonitrile:water +0.1% NH₄OH) m/z 424.1 (M-H)⁻.

EXAMPLE 30
3-{2-[4-(1-Methyl-pentyl)-phenoxy]-benzenesulfonylamino}-4-oxo-butyric acid 2-[4-(1-Methyl-pentyl)-phenoxy]-benzenesulfonyl chloride was employed to acylate the amine of Asp(OtBu)-NMe (OMe). From the resulting sulfonamide, final product was obtained as a colorless foam (158 mg, 69%) employing methods previously described. ¹H NMR (CD₃OD) as the lactol; 7.90 (m, 1H), 7.47 (m, 1H), 7.30-7.05 (m, 5H), 6.82 (d, 1H), 4.58, 4.52 (d, 1H), 3.75 (m, 1H), 2.80-2.43 (m, 3H), 1.58 (q, 2H), 1.12 (m, 7H), 0.83 (t, 3H); electrospray MS (50:50 acetonitrile:water +0.1% NH₄OH) m/z 432.1 (M-H)⁻.

EXAMPLE 31
3-[2-(4-Isopropyl-3-methyl-phenoxy)-benzenesulfonylamino]-4-oxo-butyric acid 2-(4-Isopropyl-3-methyl-phenoxy)-benzenesulfonyl chloride was employed to acylate the amine of Asp(OtBu)-NMe(OMe). From the resulting sulfonamide, final product was obtained as a colorless foam (382 mg, 79%) employing methods previously described. ¹H NMR (CD₃OD) as the lactol; 7.87 (m, 1H), 7.45 (t, 1H), 7.30 (m, 1H), 7.15 (m, 1H), 6.95 (m, 2H), 6.82 (d, 1H), 4.58, 4.52 (d, 1H), 3.75 (m, 1H), 3.17 (m, 1H), 2.57 (m, 2H), 2.33 (s, 3H), 1.23 (d, 6H); electrospray MS (50:50 acetonitrile:water +0.1% NH₄OH) m/z 404.0.1 (M-H)⁻.

EXAMPLE 32
3-(2-Benzyloxy-benzenesulfonylamino)-4-oxo-butyric acid

2-Benzyloxy-benzenesulfonyl chloride was employed to acylate the amine of Asp(OtBu)-NMe(OMe). From the resulting sulfonamide, final product was obtained as a colorless foam (137 mg, 91%) employing methods previously described. ¹H NMR (CD₃OD) as the lactol; 7.83 (m, 1H), 7.55 (m, 3H), 7.37 (m, 3H), 7.20 (m, 1H, 7.06 (m, 1H, 5.28 (s, 2H), 4.45, 4.41 (d, 1H), 3.64 (m, 1H)2.60-2.30 (m, 2H), MS APCI Probe temperature 450° C., cone voltage 25 volts, acetonitrile:methanol 4:1, 362.0 (M-H)⁻.

EXAMPLE 33
3-[2-(2,3-Dimethyl-phenoxy)-benzenesulfonylamino]-4-oxo-butyric acid 2-(2,3-Dimethyl-phenoxy)-benzenesulfonyl chloride was employed to acylate the amine of Asp(OtBu)-NMe(OMe). From the resulting sulfonamide, final product was obtained as a colorless foam (373 mg, 82%) employing methods previously described. ¹H NMR (CD₃OD) as the lactol; 7.90 (m, 1H, 7.42 (m, 1H), 7.17 (m, 3H), 6.97 (m, 1H), 6.58 (d, 1H), 4.58, 4.55 (d, 1H), 3.79 (m, 1H), 2.68-2.44 (m, 2H), 2.33 (s, 3H), 2.14 (s, 3H)MS APCI Probe temperature 450 ° C., cone voltage 25 volts, acetonitrile:methanol 4:1, 375.8 (M-H)⁻.

EXAMPLE 34
3- {2-[4-(1-Ethyl-propyl)-phenoxy]-benzenesulfonylamino}-4-oxo-butyric acid 2-[4-(1-Ethyl-propyl)-phenoxy]-benzenesulfonyl chloride was employed to acylate the amine of Asp(OtBu)-NMe (OMe). From the resulting sulfonamide, final product was obtained as a colorless foam (467 mg, 67%) employing methods previously described. ¹H NMR (CD₃OD) as the lactol; 7.92 (m, 1H), 7.45 (t, 1H), 7.17 (m, 5H), 6.83 (d, 1H, 4.58, 4.53 (d, 1H), 3.77 (m, 1H), 2.68-2.30 (m, 3H), 1.73 (m, 2H), 1.58 (m, 2H), 0.79 (t, 6H);MS APCI Probe temperature 450° C., cone voltage 25 volts, acetonitrile:methanol 4:1, 417.9 (M-H)⁻.

EXAMPLE 35
4-Oxo-3-[2-(3,4,5-trimethyl-phenoxy)-benzenesulfonylamino]-butyric acid 2-(3,4,5-trimethyl-phenoxy)-benzenesulfonyl chloride was employed to acylate the amine of Asp(OtBu)-NMe (OMe). From the resulting sulfonamide, final product was obtained as a colorless foam (407 mg, 79%) employing methods previously described. ¹H NMR (CD₃OD) as the lactol; 7.88 (m, 1H), 7.44 (t, 1H), 7.16 (m, 2H), 6.80 (m, 3H), 4.58, 4.54 (d, 1H), 3.75 (m, 1H), 2.65-2.43 (m, 2H), 2.28 (s, 6H), 2.18 (s, 3H); MS APCI Probe temperature 450° C., cone voltage 25 volts, acetonitrile:methanol 4:1, 389.8 (M-H)⁻.

EXAMPLE 36
3-(2-sec-Butoxy-benzenesulfonylamino)-4-oxo-butyric acid 2-sec-Butoxy -benzenesulfonyl chloride was employed to acylate the amine of Asp(OtBu)-NMe(OMe). From the resulting sulfonamide, final product was obtained as a colorless foam (450 mg, 73%) employing methods previously described. ¹H NMR (CD₃OD) as the lactol; 7.80 (m, 1H), 7.55 (m, 1H), 7.18 (m, 1H), 7.02 (m, 1H), 4.70 (m, 1H), 4.53, 4.42 (d, 1H), 3.65 (m, 1H), 2.45 (m, 2H), 1.88 (m, 1H), 1.75-1.38 (m, 3H), 1.38 (dd, 3H), 0.97 (dt, 3H); MS APCI Probe temperature 450° C., cone voltage 25 volts, acetonitrile:methanol 4:1, 342.1 (M-H)⁻.

EXAMPLE 37
3-[2-(4-sec-Butyl-3-methyl-phenoxy)-benzenesulfonylamino]-4-oxo-butyric acid 2-(4-sec-Butyl-3-methyl-phenoxy)-benzenesulfonyl chloride was employed to acylate the amine of Asp(OtBu)-NMe(OMe). From the resulting sulfonamide, final product was obtained as a colorless foam (257 mg, 69%) employing methods previously described. ¹H NMR (CD₃OD) as the lactol; 7.90m, 1H), 7.45 (t, 1H), 7.18 (m, 2H), 6.98 (m, 2H), 6.83 (d, 1H), 4.57, 4.53 (d, 1H), 3.75 (m, 1H), 2.94 (m, 1H), 2.58 (m, 2H), 2.32 (s, 3H), 1.63 (m, 2H), 1.21 (d, 3H), 0.86 (t, 3H); MS APCI Probe temperature 450° C., cone voltage 25 volts, acetonitrile:methanol 4:1, 420.1 (M+H)⁺.

EXAMPLE 38
3-(2-Ethylbutoxy-benzenesulfonylamino)-4-oxo-butyric acid

2-Ethylbutoxy-benzenesulfonyl chloride was employed to acylate the amine of Asp(OtBu)-NMe(OMe). From the resulting sulfonamide, final product was obtained as a colorless foam (113 mg, 51%) employing methods previously described. ¹H NMR (CD₃OD) as the lactol; 7.85 (m, 1H), 77.65 (m, 1H), 7.17 (m, 1H), 7.00 (m, 1H), 4.45, 4.35 (d, 1H), 4.05 (m, 2HO, 3.72 (m, 1H), 2.45 (m, 2H), 1.77 (m, 1H), 1.58 (m, 4H), 0.95 (t, 6H); MS APCI Probe temperature 450° C., cone voltage 25 volts, acetonitrile:methanol 4:1, 356.1 (M-H)⁻.

EXAMPLE 39
3-(2-Methylbutoxy-benzenesulfonylamino)-4-oxo-butyric acid

2-Methylbutoxy-benzenesulfonyl chloride was employed to acylate the amine of Asp(OtBu)-NMe(OMe). From the resulting sulfonamide, final product was obtained as a colorless foam (450 mg, 73%) employing methods previously described. $^1$H NMR (CD$_3$OD) as the lactol; 7.80 (m, 1H), 7.55 (m, 1H, 7.18 (m, 1H), 7.04 (m, 1H), 4.68 (m, 1H), 4.52, 4.42 (d, 1H), 3.65 (m, 1H), 2.43 (m, 2H), 1.84 (m, 1H), 1.75–1.40 (m, 3H), 1.37 (m, 3H), MS APCI Probe temperature 450° C., cone voltage 25 volts, acetonitrile:methanol 4:1, 342.1 (M-H)$^-$.

EXAMPLE 40

4-Oxo-3-[2-(1-naphthyl)ethyloxy]-benzenesulfonylamino)-butyric acid 2-(1-Naphthyl)ethyloxy-benzenesulfonyl chloride was employed to acylate the amine of Asp(OtBu)-NMe(OMe). From the resulting sulfonamide, final product was obtained as a pink foam (120 mg, 90%) employing methods previously described. $^1$H NMR (CD$_3$OD) as the lactol; 8.23 (d, 1H), 7.92 (d, 1H), 7.80 (m, 2H), 7.55 (m, 4H), 7.15 (m, 2H), 7.03 (m, 1H), 4.55 (m, 2H), 4.20, 4.03 (d, 1H, 3.74 (m, 2H), 3.60 (m, 1H, 2.44-2.10 (m, 2H); MS APCI Probe temperature 450° C., cone voltage 25 volts, acetonitrile:methanol 4:1, 428.1 (M+H)$^+$.

EXAMPLE 41

3-(2'-Methyl-biphenyl-2-sulfonylamino)-4-oxo-butyric acid

2'-Methyl-biphenyl-sulfonyl chloride was employed to acylate the amine of Asp(OtBu)-NMe(OMe). From the resulting sulfonamide, final product was obtained as a colorless foam (70 mg, 84%) employing methods previously described. $^1$H NMR (CD$_3$OD) as the lactol 8.08 (m, 1H), 7.61 (m, 1H), 7.58 (m, 1H), 7.10–7.25 (m, 5H), 4.52, 4.41 (d, 1H), 3.70 (m, 1H, 2.45 (m, 2H), 2.03 (s, 3H); MS APCI Probe temperature 450° C., cone voltage 25 volts, acetonitrile, 348.4 (M+H)$^+$.

EXAMPLE 42

3-(2-Naphthalen-1-yl-benzenesulfonylamino)-4-oxo-butyric acid

2-Naphthalen-1-yl-benzenesulfonyl chloride was employed to acylate the amine of Asp(OtBu)-NMe(OMe). From the resulting sulfonamide, final product was obtained as a colorless foam (110 mg, 71%) employing methods previously described. $^1$H NMR (CD$_3$OD) as the lactol; 8.18 (m, 1H), 7.90 (m, 2H), 7.65 (m, 2H), 7.58-7.40 (m, 3H), 7.30 (m, 3H), 4.42, 4.40 (d, 1H), 3.63 (m, 1H), 2.40 (m, 2H); MS APCI Probe temperature 450° C., cone voltage 25 volts, acetonitrile:methanol 4:1, 384.4 (M+H)$^+$.

EXAMPLE 43

3-(Naphthalene-1-sulfonylamino)-4-oxo-butyric acid

Naphthalene-1-sulfonyl chloride was employed to acylate the amine of Asp(OtBu)-NMe(OMe). From the resulting sulfonamide, final product was obtained as a colorless foam (90 mg, 66%) employing methods previously described. $^1$H NMR (CD$_3$OD) as the lactol; 8.85 (m, 1H), 8.25 (t, 1H), 8.16 (t, 1H, 8.00 (d, 1H) 7.72-7.52 (m, 3H), 4.38, 4.09 (dd, 1H, 3.67 (m, 1H), 2.80-2.22 (m, 2H); MS APCI Probe temperature 450° C., cone voltage 25 volts, acetonitrile:methanol 4:1, 308.5 (M+H)$^+$.

EXAMPLE 44

3-(3'-Methyl-biphenyl-2-sulfonylamino)-4-oxo-butyric acid

3'-Methyl-biphenyl-2-sulfonyl chloride was employed to acylate the amine of Asp(OtBu)-NMe(OMe). From the resulting sulfonamide, final product was obtained as a colorless foam (160 mg, 76%) employing methods previously described. $^1$H NMR (CD$_3$OD) as the lactol; 8.07 (m, 1H), 7.60 (m, 1H), 7.52 (m, 1H), 7.38-7.08 (m, 5H), 4.43 (m, 1H), 2.43 (m, 1H), 2.38 (s, 3H), 2.25 (m, 1H); MS APCI Probe temperature 450° C., cone voltage 25 volts, acetonitrile:methanol 4:1, 348.3 (M+H)$^+$.

EXAMPLE 45

3-[2-(Naphthalen-2-yloxy)-benzenesulfonylamino]-4-oxo-butyric acid 2-(Naphthalen-2-yloxy)-benzenesulfonyl chloride was employed to acylate the amine of Asp(OtBu)-NMe(OMe). From the resulting sulfonamide, final product was obtained as a colorless foam (60 mg, 37%) employing methods previously described. $^1$H NMR (CD$_3$OD) as the lactol; 7.98 (m, 2H), 7.87 (m, 1H, 7.81 (m, 1H), 7.60 (m, 1H, 7.45 (m, 3H), 7.38 (m, 1H), 7.20 (m, 1H), 6.90 (m, 1H), 4.60, 4.57 (d, 1H, 3.80 (m, 1H, 2.65-2.44 (m, 2H); MS APCI Probe temperature 450° C., cone voltage 25 volts, acetonitrile:methanol 4:1, 399.8 (M+H)$^+$.

EXAMPLE 46

3-(6-Methyl-biphenyl-2-sulfonylamino)-4-oxo-butyric acid

6-Methyl-biphenyl-2-sulfonyl chloride was employed to acylate the amine of Asp(OtBu)-NMe(OMe). From the resulting sulfonamide, final product was obtained as a colorless foam (120 mg, 86%) employing methods previously described. $^1$H NMR (CD$_3$OD) as the lactol; 7.92 (m, 1H, 7.52 (d, 1H, 7.40 (m, 4H), 7.30 (t, 1H), 7.20 (t, 1H), 4.46 (d, 1H, 3.65 (m, 1H, 2.52-2.32 (m, 2H), 1.98 (s, 3H); MS APCI Probe temperature 450° C., cone voltage 25 volts, acetonitrile:methanol 4:1, 348.10 (M+H)$^+$.

EXAMPLE 47

3-(3-Methyl-2-phenoxy-benzenesulfonylamino)-4-oxo-butyric acid 2-(Phenyloxy)-3-methybenzenesulfonyl chloride was employed to acylate the amine of Asp(OtBu)-NMe(OMe). From the resulting sulfonamide, final product was obtained as a colorless foam (100 mg, 55%) employing methods previously described. $^1$H NMR (CD$_3$OD) as the lactol; 7.82 (t, 1H), 7.53 (t, 1H), 7.32 (m, 1H), 7.25 (t, 2H), 7.02 (t, 1H), 6.81 (d, 2H), 4.52, 4.42 (d, 1H), 3.75 (m, 1H), 2.54 (m, 1H), 2.42 (m, 1H), 2.04 (s, 3H); MS APCI Probe temperature 450° C., cone voltage 25 volts, acetonitrile:methanol 4:1, 361.9 (M-H)$^-$.

EXAMPLE 48

4-Oxo-3-[2-phenylthio-benzenesulfonylamino]-butyric acid

2-Phenylthio-benzenesulfonyl chloride was employed to acylate the amine of Asp(OtBu)-NMe(OMe). From the resulting sulfonamide, final product was obtained as a colorless foam (140 mg, 80%) employing methods previously described. $^1$H NMR (CD$_3$OD) as the lactol; 7.95 (m, 1H), 7.69 (m, 1H), 7.44 (m, 2H), 7.35 (t, 1H), 7.27 (t, 1H), 7.00 (d, 1H), 4.56, 4.53 (d, 1H), 3.75 (m, 1H), 2.60 (m, 1H), 2.44 (m, 1H); MS APCI Probe temperature 450° C., cone voltage 25 volts, acetonitrile:methanol 4:1, 363.8 (M-H)$^-$.

EXAMPLE 49

4-Oxo-3-[2-N-phenyl-benzenesulfonylamino]-butyric acid

2-N-phenyl-benzenesulfonyl chloride was employed to acylate the amine of Asp(OtBu)-NMe(OMe). From the resulting sulfonamide, final product was obtained as a colorless foam (25 mg, 18%) employing methods previously described. $^1$H NMR (CD$_3$OD) as the lactol; 7.81 (m, 1H), 7.36 (m, 3H), 7.24 (m, 3H), 7.15 (t, 1H), 6.98 (t, 1H), 6.88 (t, 1H), 4.52, 4.45 (d, 1H), 3.65 (m, 1H), 2.62 (m, 1H), 2.38 (m, 1H); MS APCI Probe temperature 450° C., cone voltage 25 volts, acetonitrile:methanol 4:1, 347.0 (M-H)$^-$.

EXAMPLE 50
3-[2-(4-Isopropylphenoxy)-3-methylbenzenesulfonylamino]-4-oxo-butyric acid 4-Isopropylphenyloxy-3-methybenzenesulfonyl chloride was employed to acylate the amine of Asp(OtBu)-NMe(OMe). From the resulting sulfonamide, final product was obtained as a colorless foam (110 mg, 82%) employing methods previously described. $^1$H NMR (CD$_3$OD) as the lactol; 7.82 (t, 1H), 7.53 (t, 1H), 7.30 (m, 1H), 7.13 (d, 2H), 6.73 (d, 2H), 4.52, 4.42 (d, 1H), 3.74 (q, 1H), 2.58 (m, 1H), 2.42 (m, 1H), 2.03 (s, 3H), 1.20 (s, 6H); MS APCI Probe temperature 450° C., cone voltage 25 volts, acetonitrile:methanol 4:1, 406.1 (M+H)$^+$.

EXAMPLE 51
3-[2-(2-Methylphenoxy)-3-methylbenzenesulfonylamino]-4-oxo-butyric acid 2-Methylphenyloxy-3-methybenzenesulfonyl chloride was employed to acylate the amine of Asp(OtBu)-NMe(OMe). From the resulting sulfonamide, final product was obtained as a colorless foam (150 mg, 66%) employing methods previously described. $^1$H NMR (CD$_3$OD) as the lactol; 7.80 (m, 1H), 7.51 (m, 1H, 7.32 (m, 1H), 7.10 (t, 1H, 6.98 (t, 1H), 6.86 (m, 1H), 6.28 (m, 1H), 4.42, 4.28 (d, 1H, 3.68 (m, 1H), 2.58 (m, 1H), 2.44 (s, 3H), 2.38 (m, 1H), 1.95 (s, 3H); MS APCI Probe temperature 450° C., cone voltage 25 volts, acetonitrile:methanol 4:1, 378.1 (M+H)$^+$.

EXAMPLE 52
4-Oxo-3-[2-(tetrahydro-furan-2-ylmethoxy)-benzenesulfonylamino]-butyric acid 2-(Tetrahydro-furan-2-ylmethoxy)-benzenesulfonyl chloride was employed to acylate the amine of Asp(OtBu)-NMe(OMe). From the resulting sulfonamide, final product was obtained as a thick oil (0.1033 g, 15%) employing methods previously described. $^1$H NMR (CD$_3$OD, ppm) as the lactol; 7.9-7.7 (m, 1H, 7.7-7.5 (m, 1H), 7.3-7.0 (m, 2H), 4.5-4.2 (m, 3H), 4.2-3.6 (m, 4H), 2.7-2.2 (m, 2H), 2.2-1.7 (m, 4H), MS APCI Probe temperature 450° C., cone voltage 25 volts, acetonitrile:methanol 4:1, 358.1 (M+H)$^+$.

EXAMPLE 53
3-(5-Methyl-2-phenoxy-benzenesulfonylamino)-4-oxo-butyric acid

5-Methyl-2-phenoxy-benzenesulfonyl chloride was employed to acylate the amine of Asp(OtBu)-NMe(OMe). From the resulting sulfonamide, final product was obtained as a pink foam (0.2274 g, 30%) employing methods previously described. $^1$H NMR (CD$_3$OD, ppm) as the lactol; 7.73 (m, 1H), 7.5-7.0 (m, 7H), 6.76 (d, 1H), 4.5 (dd, 1H), 3.7-3.6 (m, 1H), 2.7-2.4 (m, 2H), 2.36 (s, 3H). MS APCI Probe temperature 450° C., cone voltage 25 volts, acetonitrile:methanol 4:1, 362.9 (M-H)$^-$.

EXAMPLE 54
3-(4-Methyl-2-phenoxy-benzenesulfonylamino)-4-oxo-butyric acid

4-Methyl-2-phenoxy-benzenesulfonyl chloride was employed to acylate the amine of Asp(OtBu)-NMe(OMe). From the resulting sulfonamide, final product was obtained as a colorless foam (0.1279 g, 15%) employing methods previously described. $^1$H NMR (CD$_3$OD, ppm) as the lactol; 7.8 (m, 1H), 7.4 (m, 2H), 7.3-6.9 (m, 4H), 6.65 (s, 1H), 4.5 (dd, 1H), 3.7 (m, 1H), 2.7-2.4 (m, 2H), 2.28 (s, 3H). MS APCI Probe temperature 450° C., cone voltage 25 volts, acetonitrile:water 4:1, 364.1 (M+H)$^+$.

EXAMPLE 55
3-(2-Nitro-benzenesulfonylamino)-4-oxo-butyric acid

2-Nitro-benzenesulfonyl chloride was employed to acylate the amine of Asp(OtBu)-NMe(OMe). From the resulting sulfonamide, final product was obtained as a thick yellow oil (0.028 g, 4%) employing methods previously described. $^1$H NMR (CD$_3$OD, ppm) as the lactol; 8.11 (m, 1H), 7.88 (m, 1H), 7.79 (m, 2H), 4.50 (m, 1H), 3.83 (m, 1H), 2.7-2.4 (m, 2H). MS APCI Probe temperature 450° C., cone voltage 25 volts, acetonitrile:water 4:1, 301.9 (M)$^-$.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for modulating responsiveness to a corticosteroid in a subject, comprising administering to the subject suffering from a condition normally responsive to corticosteroid therapy:
   an interleukin-1 β converting enzyme (ICE) inhibitor being administered at a dosage and by a route sufficient to inhibit production of IFN-γ in the subject; and
   a corticosteroid,
such that responsiveness of the subject to the corticosteroid is modulated as compared to when a corticosteroid alone is administered to the subject.

2. The method of claim 1, wherein the ICE inhibitor is an IFN-γ inducing factor (IGIF) antagonist, the ICE inhibitor being administered at a dosage and by a route sufficient to inhibit IGIF activity in the subject.

3. The method of claim 1, wherein the corticosteroid is selected from the group consisting of cortisone, hydrocortisone, beclomethasone, flunisolide, prednisone, prednisolone, methylprednisolone, triamcinolone, deflazacort, betamethasone and dexamethasone.

4. The method of claim 1, wherein the subject is suffering from septic shock.

5. The method of claim 1, wherein the subject is suffering from Crohn's disease.

6. The method of claim 1, wherein the subject is suffering from asthma.

7. The method of claim 1, wherein the subject is suffering from graft versus host disease or transplant rejection.

8. The method of claim 1, wherein the subject is suffering from an autoimmune disease or disorder.

9. The method of claim 1, wherein the subject is suffering from an immunoinflammatory disease or disorder selected from the group consisting of asthma, adult respiratory distress syndrome, systemic lupus erythematosus, inflammatory bowel disease, Crohn's disease, ulcerative colitis, multiple sclerosis, insulin-dependent diabetes mellitus, autoimmune arthritis, rheumatoid arthritis, juvenile rheumatoid arthritis, psoriatic arthritis, inflammatory pulmonary syndrome, pemphigus vulgaris, idiopathic thrombocytopenic purpura, autoimmune meningitis, myasthenia gravis, autoimmune thyroiditis, dermatitis, atopic dermatitis, eczematous dermatitis, psoriasis, Sjögren's Syndrome, keratoconjunctivitis sicca secondary to Sjögren's Syndrome, alopecia areata, allergic responses due to arthropod bite reactions, aphthous ulcer, iritis, conjunctivitis, keratoconjunctivitis, cutaneous lupus erythematosus, scleroderma, vaginitis, proctitis, drug eruptions, Stevens-Johnson syndrome, leprosy reversal reactions, erythema nodosum leprosum, autoimmune uveitis, allergic encephalomyelitis, aplastic anemia, pure red cell anemia, idiopathic thrombocytopenia, polychondritis, Wegener's granulomatosis, chronic active hepatitis, Graves ophthalmopathy, primary biliary cirrhosis, uveitis posterior and interstitial lung fibrosis.

10. The method of claim 1, wherein the subject is suffering from an acute inflammatory disorder.

11. The method of claim 1, wherein the subject is suffering from a chronic inflammatory disorder.

12. The method of claim 1, wherein the ICE inhibitor and corticosteroid are administered such that steroid resistance in the subject is reversed, as compared to when a corticosteroid alone is administered to the subject.

13. The method of claim 1, wherein the ICE inhibitor and corticosteroid are administered such that steroid sensitivity in the subject is increased, as compared to when a corticosteroid alone is administered to the subject.

14. The method of claim 1, wherein the ICE inhibitor and the corticosteroid are administered to the subject according to a schedule that reduces the dosage of the corticosteroid over time and e method ameliorates a steroid rebound effect associated with administration of reduced dosages of the corticosteroid.

15. A method for modulating responsiveness to corticosteroids in a subject, comprising administering to the subject suffering from a condition normally responsive to corticosteroid therapy, an interleukin-1 β converting enzyme (ICE) inhibitor; and
a corticosteroid, such that responsiveness of the subject to the corticosteroid is modulated as compared to when a corticosteroid alone is administered to the subject.

16. The method of claim 15, wherein the corticosteroid is selected from the group consisting of cortisone, hydrocortisone, beclomethasone, flunisolide, prednisone, prednisolone, methylprednisolone, triamcinolone, deflazacort, betamethasone and dexamethasone.

17. The method of claim 15, wherein the subject is suffering from septic shock.

18. The method of claim 15, wherein the subject is suffering from Crohn's disease.

19. The method of claim 15, wherein the subject is suffering from asthma.

20. The method of claim 15, wherein the subject is suffering from graft versus host disease or transplant rejection.

21. The method of claim 15, wherein the subject is suffering from an autoimmune disease or disorder.

22. The method of claim 15, wherein the subject is suffering from an immunoinflammatory disease or disorder selected from the group consisting of asthma, adult respiratory distress syndrome, systemic lupus erythematosus, inflammatory bowel disease, Crohn's disease, ulcerative colitis, multiple sclerosis, insulin-dependent diabetes mellitus, autoimmune arthritis, rheumatoid arthritis, juvenile rheumatoid arthritis, psoriatic arthritis, inflammatory pulmonary syndrome, pemphigus vulgaris, idiopathic thrombocytopenic purpura, autoimmune meningitis, myasthenia gravis, autoimmune thyroiditis, dermatitis, atopic dermatitis, eczematous dermatitis, psoriasis, Sjögren's Syndrome, keratoconjunctivitis sicca secondary to Sjögren's Syndrome, alopecia areata, allergic responses due to arthropod bite reactions, aphthous ulcer, iritis, conjunctivitis, keratoconjunctivitis, cutaneous lupus erythematosus, scleroderma, vaginitis, proctitis, drug eruptions, Stevens-Johnson syndrome, leprosy reversal reactions, erythema nodosum leprosum, autoimmune uveitis, allergic encephalomyelitis, aplastic anemia, pure red cell anemia, idiopathic thrombocytopenia, polychondritis, Wegener's granulomatosis, chronic active hepatitis, Graves ophthalmopathy, primary biliary cirrhosis, uveitis posterior and interstitial lung fibrosis.

23. The method of claim 15, wherein the subject is suffering from an acute inflammatory disorder.

24. The method of claim 15, wherein the subject is suffering from a chronic inflammatory disorder.

25. The method of claim 24, wherein the ICE inhibitor and the corticosteroid are administered such that steroid resistance in the subject is reversed, as compared to when a corticosteroid alone is administered to the subject.

26. The method of claim 24, wherein the ICE inhibitor and the corticosteroid are administered such that steroid sensitivity in the subject is increased, as compared to when a corticosteroid alone is administered to the subject.

27. The method of claim 24, wherein the ICE inhibitor and the corticosteroid are administered to the subject according to a schedule that reduces the dosage of the corticosteroid over time and the method ameliorates a steroid rebound effect associated with administration of reduced dosages of the corticosteroid.

28. A method for modulating responsiveness to a corticosteroid in a subject, comprising:

selecting a subject in need of modulation of responsiveness to a corticosteroid, wherein the subject suffers from a condition normally responsive to corticosteroid therapy; and administering to the subject an interleukin-1 β converting enzyme (ICE) inhibitor which antagonizes a factor that regulates production of interferon (IFN-γ) in the subject, the ICE inhibitor being administered at a dosage and by a route sufficient to inhibit production of IFN-γ in the subject, such that responsiveness of the subject to a corticosteroid is modulated as compared to when a corticosteroid alone is administered to the subject.

29. The method of claim 28, wherein the subject is resistant to a corticosteroid prior to administration of the ICE inhibitor.

30. The method of claim 28, wherein the subject is responsive to a corticosteroid prior to administration of the ICE inhibitor but exhibits increased sensitivity to the corticosteroid after administration of the ICE inhibitor.

31. The method of claim 28, wherein treatment of the subject with a corticosteroid is to be stopped and administration of the ICE inhibitor ameliorates a steroid rebound effect in the subject.

32. The method of claim 28, wherein the ICE inhibitor is an IFN-γ inducing factor (IGIF) antagonist, the ICF inhibitor being administered at a dosage and by a route sufficient to inhibit IGIF activity in the subject.

33. A method for modulating responsiveness to corticosteroids in a subject comprising administering to the subject suffering from a condition normally responsive to corticosteroid therapy:

an interleukin-1β converting enzyme (ICE) inhibitor compound having the structure of Formula I:

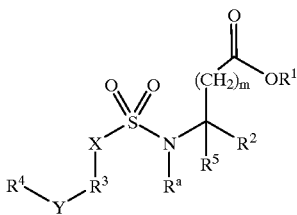

wherein
R$^1$ is hydrogen, C$_1$–C$_6$alkyl, or benzyl;
R$^2$ is —CHO, —COR$^a$, or —CN;
each R$^a$ is independently hydrogen or C$_1$–C$_6$alkyl;
X is a bond, CH$_2$, CHR$^5$, NH, NR$^5$, or O;
R$^3$ is aryl, substituted-aryl, heteroaryl, substituted-heteroaryl, cycloalkyl, substituted-cycloalkyl, heterocycle, or substituted-heterocycle;
Y is absent, NR$^5$, CO, S, O, SO$_2$, —O(CHR$^5$)$_n$—, CHR$^5$, NR$^5$CO, NC(O)R$^5$, CONR$^5$, OCHR$^5$, CHR$^5$O, SCHR$^5$, CHR$^5$S, SO$_2$NR$^5$, C$_1$–C$_6$alkyl, NR$^5$SO$_2$, CH$_2$CHR$^5$, CHR$^5$CH$_2$, COCH$_2$, or CH$_2$CO;
R$^4$ is absent, aryl, substituted-aryl, C$_1$–C$_8$alkyl, heteroaryl, substituted-heteroaryl, cycloalkyl, C$_1$–C$_6$alkyl, substituted-cycloalkyl, heterocycloalkyl, or substituted-heterocycloalkyl;
each R$^5$ is independently hydrogen, C$_1$–C$_6$alkyl, aryl, —(CH$_2$)$_n$aryl, or —(CH$_2$)$_n$cycloalkyl;
each n is independently 0 to 5, m is 1 or 2, and the pharmaceutically acceptable salts, esters, amides, and prodrugs thereof; and
a corticosteroid,
such that responsiveness of the subject to the corticosteroid is modulated as compared to when a corticosteroid alone is administered to the subject.

34. A method for modulating responsiveness to a corticosteroid in a subject, comprising:
selecting a subject in need of modulation of responsiveness to a corticosteroid, wherein the subject suffers from a condition normally responsive to corticosteroid therapy; and
administering to the subject an interleukin-1β converting enzyme (ICE) inhibitor compound having The structure of Formula I:

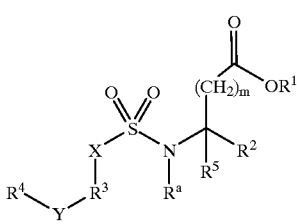

wherein
R$^1$ is hydrogen, C$_1$–C$_6$alkyl, or benzyl;
R$^2$ is —CHO, —COR$^a$, or —CN;
each R$^a$ is independently hydrogen or C$_1$–C$_6$alkyl;
X is a bond, CH$_2$, CHR$^5$, NH, NR$^5$, or O;
R$^3$ is aryl, substituted-aryl, heteroaryl, substituted-heteroaryl, cycloalkyl, substituted-cycloalkyl, heterocycle, or substituted-heterocycle;

Y is absent, NR$^5$, CO, S, O, SO$_2$, —O(CHR$^5$)$_n$—, CHR5, NR$^5$CO, NC(O)R$^5$, CONR$^5$, OCHR$^5$, CHR$^5$O, SCHR$^5$, CHR$^5$S, SO$_2$NR$^5$, C$_1$–C$_6$alkyl, NR$^5$SO$_2$, CH$_2$CHR$^5$, CHR$^5$CH$_2$, COCH$_2$, or CH$_2$CO;
R$^4$ is absent, aryl, substituted-aryl, C$_1$–C$_8$alkyl, heteroaryl, substituted-heteroaryl, cycloalkyl, C$_1$–C$_6$alkyl, substituted-cycloalkyl, heterocycloalkyl, or substituted-heterocycloalkyl;
each R$^5$ is independently hydrogen, C$_1$–C$_6$alkyl, aryl, —(CH$_2$)$_n$aryl, or —(CH$_2$)$_n$cycloalkyl;
each n is independently 0 to 5, m is 1 or 2, and the pharmaceutically acceptable salts, esters, amides, and prodrugs thereof,
the compound being administered at a dosage and by a route sufficient to inhibit production of IFN-γ in the subject,
such that responsiveness of the subject to a corticosteroid is modulated as compared to when a corticosteroid alone is administered to the subject.

35. A method of claim 9, wherein the subject is suffering from an immunoinflammatory disease or disorder selected from the group consisting of pemphigus vulgaris, dermatitis, atopic dermatitis, eczematous dermatitis, psoriasis, alopecia areata, allergic responses due to arthropod bite reactions, cutaneous lupus erythematosus, scleroderma, vaginitis, drug eruptions, Stevens-Johnson syndrome, leprosy reversal reactions, and erythema nodosum leprosum.

36. A method of claim 9, wherein the subject is suffering from an immunoinflammatory disease or disorder selected from the group consisting of multiple sclerosis, autoimmune arthritis, rheumatoid arthritis, juvenile rheumatoid arthritis, psoriatic arthritis, autoimmune meningitis, myasthenia gravis and allergic encephalomyelitis.

37. A method of claim 9, wherein the subject is suffering from an immunoinflammatory disease or disorder selected from the group consisting of systemic lupus erythematosus, inflammatory bowel disease, Crohn's disease, ulcerative colitis, insulin-dependent diabetes mellitus, aphthous ulcer, proctitis, Wegener's granulomatosis, chronic active hepatitis, and primary biliary cirrhosis.

38. A method of claim 9, wherein the subject is suffering from an immunoinflammatory disease or disorder selected from the group consisting of iritis, conjunctivitis, keratoconjunctivitis, autoimmune uveitis, Graves ophthalmopathy, and uveitis posterior.

39. A method of claim 9, wherein the subject is suffering from an immunoinflammatory disease or disorder selected from the group consisting of idiopathic thrombocytopenic purpura, autoimmune thyroiditis, Sjögren's Syndrome, keratoconjunctivitis sicca secondary to Sjögren's Syndrome, aplastic anemia, pure red cell anemia, idiopathic thrombocytopenia, and polychondritis.

40. The method of claim 9, wherein the subject is suffering from an immunoinflammatory disease or disorder selected from the group consisting of asthma, adult respiratory distress syndrome, inflammatory pulmonary syndrome, and interstitial lung fibrosis.

41. A method of claim 22, wherein the subject is suffering from an immunoinflammatory disease or disorder selected from the group consisting of pemphigus vulgaris, dermatitis, atopic dermatitis, eczematous dermatitis, psoriasis, alopecia areata, allergic responses due to arthropod bite reactions, cutaneous lupus erythematosus, scleroderma, vaginitis, drug eruptions, Stevens-Johnson syndrome, leprosy reversal reactions, and erythema nodosum leprosum.

42. A method of claim 22, wherein the subject is suffering from an immunoinflammatory disease or disorder selected from the group consisting of mutiple sclerosis, autoimmune arthritis, rheumatoid arthritis, juvenile rheumatoid arthritis, psoriatic arthritis, autoimmune meningitis, myasthenia gravis and allergic encephalomyelitis.

43. A method of claim 22, wherein the subject is suffering from an innumoinflammatory disease or disorder selected from the group consisting of systemic lupus erythematosus, inflammatory bowel disease, Crohn's disease, ulcerative colitis, insulin-dependent diabetes mellitus, aphthous ulcer, procitis, Wegener's granulomatosis, chronic active hepatitis, and primary biliary cirrhosis.

44. A method of claim 22, wherein the subject is suffering from an inflammatory disease or disorder selected from the group consisting of ireitis, conjunctivitis, keratoconjunctivitis, autoimmune eveitis, Graves ophthalmopathy, and uveitis posterior.

45. A method of claim 22, wherein the subject is suffering from an immunoinflammatory disease or disorder selected from the group consisiting of idiopathic thrombocytopenic purpura, autoimmune thyroiditis, Sjögren's Syndrome, keratoconjunctivitis sicca secondary to Sjögren's Syndrome, aplastic anemia, pure red cell anemia, idiopathic thrombocytopenia, and polychondritis.

46. The method of claim 22, wherein the subject is suffering from an immunoinflammatory disease or disorder selected from the group consisting of asthma, adult respiratory distress syndrome, inflammatory pulmonary syndrome, and interstitial lung fibrosis.

* * * * *